(12) United States Patent
Santamaria et al.

(10) Patent No.: US 11,733,189 B2
(45) Date of Patent: Aug. 22, 2023

(54) METHOD FOR IDENTIFYING A BLEND OF NUCLEATORS USEFUL FOR PREPARING A NUCLEATED POLYOLEFIN MATERIAL

(71) Applicant: NJC Europe Limited, Oldham (GB)

(72) Inventors: Estibaliz Santamaria, Oldham (GB); Hieu-Dinh Phan, Oldham (GB); Sukehiro Niga, Kyoto (JP); Yohei Uchiyama, Kyoto (JP)

(73) Assignee: NJC EUROPE LIMITED, Oldham (GB)

( * ) Notice: Subject to any disclaimer, the term of this patent is extended or adjusted under 35 U.S.C. 154(b) by 1159 days.

(21) Appl. No.: 16/095,203

(22) PCT Filed: Apr. 19, 2017

(86) PCT No.: PCT/GB2017/051093
§ 371 (c)(1),
(2) Date: Apr. 4, 2019

(87) PCT Pub. No.: WO2017/182804
PCT Pub. Date: Oct. 26, 2017

(65) Prior Publication Data
US 2019/0219528 A1    Jul. 18, 2019

(30) Foreign Application Priority Data
Apr. 19, 2016 (GB) .................................. 1606828

(51) Int. Cl.
*G01N 25/48* (2006.01)
*C08K 5/1575* (2006.01)
(Continued)

(52) U.S. Cl.
CPC ......... *G01N 25/482* (2013.01); *C08K 5/0083* (2013.01); *C08K 5/1575* (2013.01);
(Continued)

(58) Field of Classification Search
CPC ............... G01N 25/482; G01N 21/171; G01N 21/1717; G01N 25/04; G01N 33/442;
(Continued)

(56) References Cited

U.S. PATENT DOCUMENTS 5,015,684 A * 5/1991 Kobayashi ........... C08K 5/0083
524/108
5,470,898 A * 11/1995 Syed .................... C08K 5/1575
524/84
(Continued)

FOREIGN PATENT DOCUMENTS

CA   2137960 C * 5/2006 ............. C08L 23/10
CN   1241190 A * 1/2000 ........... C07D 493/04
(Continued)

OTHER PUBLICATIONS

International Application No. PCT/GB2017/051093 Search Report, ISA/EPO dated Jul. 7, 2017.
(Continued)

*Primary Examiner* — Mohamed K Amara
(74) *Attorney, Agent, or Firm* — Stephen Y. Liu; David W. Carstens; Carstens, Allen & Gourley, LLP

(57) ABSTRACT

The present invention relates to a method for identifying a blend of nucleators with reduced haze in nucleated polyolefin material compared to blends of the same nucleators having different component weight ratios. The method comprises:
i) preparing multiple blends of at least two nucleators wherein each blend containing the same nucleators in different weight ratios, wherein the blends include one or more blends in which one of the nucleators is a major weight fraction and one or more blends where the same nucleator is a minor weight fraction;
ii) determining, for each blend, a minimum dissolution temperature when the blend completely dissolves in
(Continued)

Figure 1:
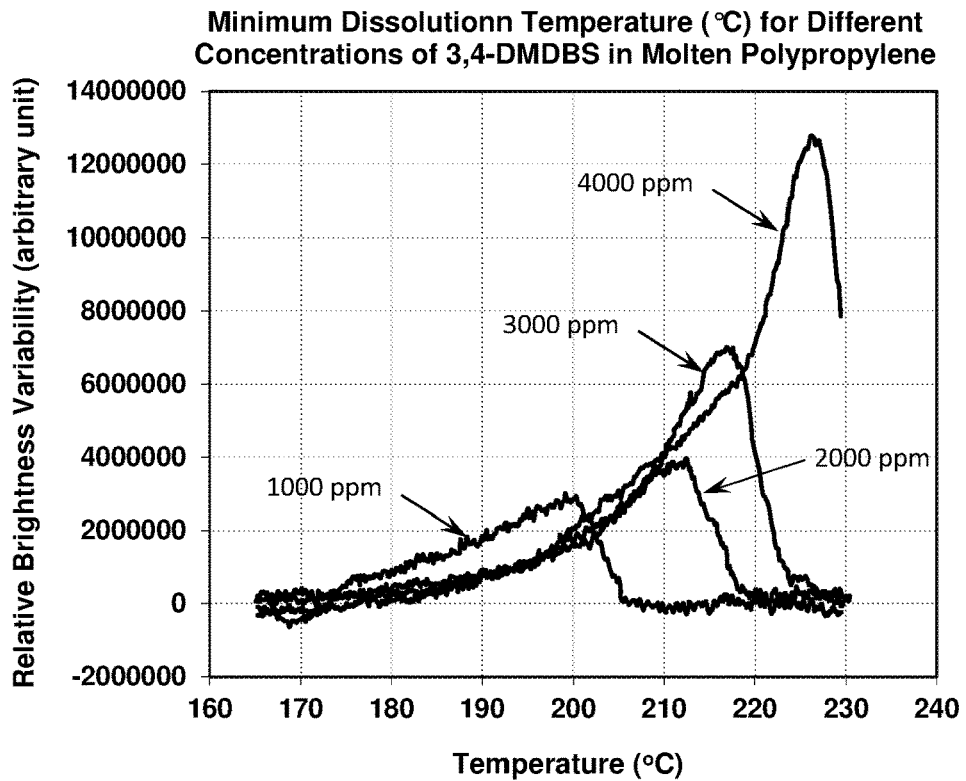

individual samples of the same molten polyolefin resin, wherein the concentration of each blend is substantially the same and below the saturation point in the molten polyolefin resin; and iii) identifying a blend that has a lower minimum dissolution temperature than the majority of the blends.

20 Claims, 4 Drawing Sheets

(51) Int. Cl.
| | | |
|---|---|---|
| *G01N 21/17* | (2006.01) | |
| *G01N 25/04* | (2006.01) | |
| *C08K 5/00* | (2006.01) | |
| *C08L 23/14* | (2006.01) | |
| *G01N 33/44* | (2006.01) | |

(52) U.S. Cl.
CPC ............ *C08L 23/14* (2013.01); *G01N 21/171* (2013.01); *G01N 21/1717* (2013.01); *G01N 25/04* (2013.01); *C08L 2205/24* (2013.01); *G01N 33/442* (2013.01); *G01N 2021/1744* (2013.01); *G01N 2021/1761* (2013.01); *G01N 2021/1765* (2013.01)

(58) Field of Classification Search
CPC ... G01N 2021/1744; G01N 2021/1761; G01N 2021/1765; C08K 5/0083; C08K 5/1575; C08K 5/20; C08K 2201/014; C08L 23/14; C08L 2205/24; C08L 23/00; C08L 23/02; C08L 23/10; C08L 23/12; C08L 2666/02; C08J 2323/12; H01M 50/417
See application file for complete search history.

(56) References Cited

U.S. PATENT DOCUMENTS

| | | | | |
|---|---|---|---|---|
| 6,245,843 | B1* | 6/2001 | Kobayashi | ............ C08K 5/1575 |
| | | | | 524/109 |
| 6,989,154 | B2 | 1/2006 | Lake et al. | |
| 7,351,758 | B2 | 4/2008 | Xu et al. | |
| 7,501,462 | B2 | 1/2009 | Xu et al. | |
| 2002/0161076 | A1 | 10/2002 | Lake, Jr. et al. | |
| 2004/0007794 | A1* | 1/2004 | Morin | ...................... C08K 5/49 |
| | | | | 264/210.8 |
| 2005/0075433 | A1* | 4/2005 | Mannion | ............... C08K 5/0083 |
| | | | | 524/285 |
| 2006/0122294 | A1* | 6/2006 | Beuke | .................. C08K 5/1575 |
| | | | | 524/109 |
| 2006/0189744 | A1* | 8/2006 | Tse | ........................... C08L 23/20 |
| | | | | 524/451 |
| 2006/0270766 | A1 | 11/2006 | Xu et al. | |
| 2008/0045638 | A1* | 2/2008 | Chapman | ................. C08L 23/10 |
| | | | | 524/425 |
| 2012/0028006 | A1 | 2/2012 | Yamaguchi et al. | |
| 2014/0221515 | A1* | 8/2014 | Datta | ..................... C08J 9/0061 |
| | | | | 521/110 |
| 2015/0228376 | A1* | 8/2015 | Ranganathan | .......... C08L 23/12 |
| | | | | 428/375 |
| 2017/0240721 | A1* | 8/2017 | Santamaria | .......... C08K 5/1575 |
| 2017/0369611 | A1* | 12/2017 | Huang | ................. C08K 5/0083 |
| 2018/0371126 | A1* | 12/2018 | Wang | ...................... C08F 2/001 |
| 2020/0325290 | A1* | 10/2020 | Schmitt | ................... B32B 27/32 |
| 2021/0017368 | A1* | 1/2021 | Gahleitner | ............ C08F 210/06 |
| 2022/0010114 | A1* | 1/2022 | Klimke | ............... B29C 49/0005 |
| 2022/0227983 | A1* | 7/2022 | Wang | .................... C08F 210/06 |

FOREIGN PATENT DOCUMENTS

| | | | | |
|---|---|---|---|---|
| CN | 101278002 | A * | 10/2008 | .......... C08K 5/0083 |
| CN | 101338056 | A | 1/2009 | |
| CN | 102816377 | A | 12/2012 | |
| CN | 105524356 | A | 4/2016 | |
| EP | 1365741 | A1 | 9/2002 | |
| EP | 1401938 | B1 * | 2/2010 | ............. C08K 5/098 |
| GB | 2531301 | A | 4/2016 | |
| JP | S6341551 | A | 2/1988 | |
| JP | H08325415 | A | 12/1996 | |
| JP | 2004524417 | A * | 8/2004 | ............ C08L 101/00 |
| WO | WO2006127235 | A2 | 11/2006 | |

OTHER PUBLICATIONS

GB Application No. 1606828.0 Search Report, GB Intellectual Property Office dated Jan. 11, 2017.
Zsuzsanna Horvath, et al.; "The role of solubility and critical temperatures for the efficiency of sorbitol clarifiers in polypropylene"; Journal of The Royal Society of Chemistry 2014; RSC Adv., 2014, 4, pp. 19737-19745.
Magnus Kristiansen, et al.; "The Binary System Isotactic Polypropylene/Bis(3,4-dimethylbenzylidene)sorbitol: Phase Behavior, Nucleation, and Optical Properties"; Macromolecules 2003, 36, pp. 5150-5156.
P.H. Karpinski et al.; "Preceipitation Processes"; The Handbook of Industrial Crystsallization, Second Edition, 2002, Chapter 6; pp. 141-160.
"Optical brighteners: improving the colour of plastics"; Plastics, Additives and Compounding, vol. 5, Issue 6, Jun. 2003, pp. 42-46.
Alfred G. Oertli; "Fluorescent Whitening Agents"; Plastics Additives Handbook, Hanser Gardner Publications, 6th Edition, 2009; Chapter 16 pp. 901-906.

* cited by examiner

METHOD FOR IDENTIFYING A BLEND OF NUCLEATORS USEFUL FOR PREPARING A NUCLEATED POLYOLEFIN MATERIAL

CROSS REFERENCE TO RELATED APPLICATIONS

This application is the U.S. national phase of International Application No. PCT/GB2017/051093 filed Apr. 19, 2017, which designated the U.S. and claims priority to GB application number 1606828.0 filed Apr. 19, 2016, the entire content of which is hereby incorporated by reference.

The present invention relates to a method for identifying a blend of nucleators which is advantageous for preparing a nucleated polyolefin material. In particular, the method of the invention is useful for identifying a blend of least two nucleators having a weight ratio of components that provides reduced haze in a nucleated polyolefin material compared to blends of the same nucleators having different weight ratios of components. The present invention also relates to methods wherein the identified blend is used for preparing a nucleated polyolefin material.

Nucleating agents are well known for their use in modifying the crystallization process of polyolefin resins. Such compounds are known to: shorten cycle times (i.e. the time required to mould a single plastic part), as a result of more rapid solidification; improve mechanical properties, such as stiffness and heat resistance; and improve the optical properties of plastics, such as haze level, by eliminating large spherulites which scatter light. These effects have, inter alia, allowed polypropylene and linear low density polyethylene plastics prepared with nucleating and clarifying agents to be used in place of expensive polyethylene terephthalate or polystyrene for containers and packaging products which require good optical clarity.

In contrast to metal salts and the like, where nucleators are soluble in polyolefin resins, preparation of a nucleated polyolefin material typically requires that the nucleator be dissolved in the molten resin. Subsequent recrystallization of the soluble nucleator forms a fine crystalline network providing nucleation sites, which reduce the size of spherulites formed in the resin as it cools, thereby reducing light scattering and improving clarity. In conventional molding methods comprising the step of injecting or extruding a polyolefin resin containing a nucleator, the temperature of the molten resin is appreciably higher than the sol-gel transition temperature of the melt during the heating cycle. Furthermore, use of a nucleator having a high melting point can have the disadvantage that the resin composition containing it must be molded at commensurately high temperatures in order to solubilize the nucleator, leading to significant energy consumption.

For example, a crystalline resin composition containing as a nucleator either 1,3:2,4-bis(polyalkylbenzene)sorbitol or an unsymmetrical dibenzylidene sorbitol (DBS) derivative (wherein the two aromatic rings have different substituents) may provide a molded article exhibiting desirable optical properties. However the melting point of such nucleators is as high as 260° C., and so the resin composition must typically be processed at a correspondingly high temperature, so as to obtain adequate dissolution of the nucleator in the resin composition. If processing temperatures are too low, insufficient dissolution of the nucleator will result; leading to unsatisfactory levels of haze in the resulting polyolefin material.

As processing temperature is increased to accommodate such high melting point nucleators, energy consumption is also increased, undesirably. Furthermore, the cycle time for processing the plastic article may also be lengthened as a result of longer cooling periods. This negates advances continuously being made in lowering the temperature profiles of polyolefin resins, particularly polypropylene, such that melting temperatures are lowered and brought closer to crystallisation temperatures, which can reduce cooling periods and therefore cycle times. High processing temperatures can in effect preclude the economic viability of plastics preparation. Additionally, another problem that may arise with high processing temperatures is that nucleators can sublimate when heated to temperatures near their melting points, for instance during the high temperature moulding operation, leading to unwanted re-deposition on moulding equipment (i.e. "plate-out").

Efforts have been made to identify blends or combinations of nucleating agents as a means for obtaining satisfactory clarity in a polyolefin material but at lower processing temperatures. For instance, a particularly preferred, but high cost, DBS derivative having a high nucleating efficiency and affording good organoleptic properties is bis-3,4-dimethylbenzylidene sorbitol (3,4-DMDBS). However, the use of 3,4-DMDBS requires high processing temperatures, otherwise there is a problem of unacceptable levels of haze in polyolefin articles prepared with this agent when processing temperatures are lower than 230° C. U.S. Pat. No. 7,351,758 and its corresponding continuation, U.S. Pat. No. 7,501,462, describe using a blend of 3,4-DMDBS and DBS (unsubstituted) nucleating agents to try and address this issue. However, improvements at lower processing temperatures, for example below 210° C., were only observed with polypropylene resins exhibiting high melt flow values of at least 20, preferably at least 50: which require the use of a "visbreaking agent" in order to reduce the viscosity of the polyolefin resin and increase the melt flow index.

U.S. Pat. No. 6,989,154 discloses a blend of 3,4-DMDBS and p-methyldibenzylidene sorbitol (MDBS) as a lower cost alternative to using 3,4-DMDBS alone as a nucleating and clarifying agent. It is reported that the blend confers a good degree of clarification in terms of the haze level in polyolefin articles prepared using the blend. However, U.S. Pat. No. 6,989,154 teaches that the blend of 3,4-DMDBS and MDBS must be used in a resin composition processed at conventional high processing temperatures. Indeed, according to the example described in the experimental section of U.S. Pat. No. 6,989,154, the melt temperature of the resin and additive composition upon exit of the extruder die was as high as 246° C., whilst the moulder barrel was reportedly set to 220° C.

U.S. Pat. No. 6,989,154 also describes alternative blends, including: 3,4-DMDBS/DBS; 3,4-DMDBS/EDBS; or 3,4-DMDBS/TDBS (1,3;2,4-bis(5', 6', 7', 8'-tetrahydro-2-naphthylidene) sorbitol). However, these blends are reported not to exhibit any of the benefits of the 3,4-DMDSS/MDBS blend, as illustrated in results of the comparative examples in Table 2 of that document, which were processed under similarly high processing temperatures.

Royal Society of Chemistry Advances, 2014, 4, 19737-19745, describes the role of solubility on the efficiency of sorbitol clarifiers in polypropylene. This document discusses transformations in the crystal structures of sorbitol derivatives at elevated temperatures which can aid dissolution of the sorbitol derivative in the polypropylene resin. This is thought to enable appreciable dissolution, and effective nucleation, below the melting point of the sorbitol derivative and offers an explanation as to why processing temperatures much lower than the melting point of the sorbitol derivative can be used whilst still obtaining satisfactory haze level and clarity in the resulting polyolefin material. This document does not provide any information regarding blends of different nucleators or the effect of combinations of nucleators on nucleator solubility in the polyolefin resin.

There remains a need for a reliable method for identifying blends of nucleators of a particular weight ratio which can effectively broaden the range of temperature over which nucleated polyolefin materials may be prepared by lowering the effective minimum processing temperature, without compromising haze values or organoleptic properties.

The present invention is based on the discovery that increasing the solubility of a blend of nucleators in the polyolefin resin leads to improvements in the haze value and optical properties of the nucleated polyolefin material obtained therefrom. Additionally, it has also been surprisingly found that the solubility of blends of different nucleators in a polyolefin resin can change unpredictably by adjusting the weight ratio of the components of the blend. For instance, particular weight ratios of nucleators of a blend have been found by the inventors to result in a surprising synergy between components leading to improved solubility properties in comparison to those of the components individually. By identifying a blend having a particular weight ratio of components which has a higher solubility in the polyolefin resin than blends of the same nucleators having different weight ratios of the components, it is possible to obtain a nucleated polyolefin material having good haze and optical properties which is obtainable at lower processing temperatures than would otherwise be possible.

Thus, in a first aspect, the present invention provides a method for identifying a blend of at least two nucleators having a weight ratio of components that provides reduced haze in a nucleated polyolefin material compared to blends of the same nucleators having different weight ratios of components, wherein each nucleator is soluble in a molten polyolefin resin, said method comprising the steps of:
  i) preparing a plurality of blends of the at least two nucleators wherein each blend contains the same at least two nucleators but in a different weight ratio, wherein the plurality of blends includes one or more blends in which one of the at least two nucleators is a major weight fraction of the blend as well as one or more blends in which the same one of the at least two nucleators is a minor weight fraction of the blend;
  ii) determining, for each of the blends prepared in step i), a minimum dissolution temperature at which a given concentration of each of the blends becomes completely dissolved in individual samples of the same molten polyolefin resin, wherein the concentration of each of the different blends in the individual samples is substantially the same and below the saturation point in the molten polyolefin resin and the same method for determining the minimum dissolution temperature is used for each blend; and
  iii) identifying a blend of the at least two nucleators which has a minimum dissolution temperature which is lower than that determined in step ii) for a majority of the plurality of blends.

In an second aspect, the present invention provides a method for identifying a blend of at least two nucleators having a weight ratio of components that provides reduced haze in a nucleated polyolefin material compared to blends of the same nucleators having different weight ratios of components, wherein each nucleator is soluble in a molten polyolefin resin, said method comprising the steps of:
  i) preparing a plurality of blends of the at least two nucleators wherein each blend contains the same at least two nucleators but in a different weight ratio, wherein each of the plurality of blends of the at least two nucleators includes the same one nucleator as a major weight fraction of the blend;
  ii) determining, for each of the blends prepared in step i), a minimum dissolution temperature at which a given concentration of each of the blends becomes completely dissolved in individual samples of the same molten polyolefin resin, wherein the concentration of each of the different blends in the individual samples is substantially the same and below the saturation point in the molten polyolefin resin and the same method for determining the minimum dissolution temperature is used for each blend; and
  iii) identifying a blend of the at least two nucleators which has a minimum dissolution temperature which is lower than that determined in step ii) for a majority of the plurality of blends.

The methods according to the present invention involve the determination of the minimum dissolution temperature for a given concentration of a blend of nucleators in a polyolefin resin. Reference herein to the "minimum dissolution temperature" is intended to refer to the minimum temperature at which nucleating agents and blends thereof become completely dissolved in a molten polyolefin resin.

As the skilled person will appreciate, the nucleators used in the present invention are suitable for nucleating a polyolefin material. Furthermore, since the method involves the determination of a minimum temperature at which the blend of nucleators becomes completely dissolved in the polyolefin resin, it will also be appreciated that the blend of nucleators exhibits solubility in molten polyolefin resin, at least up to a saturation point. Therefore, the concentration of the nucleators which is used to determine the minimum dissolution temperature in accordance with the present invention is below the saturation point of the nucleators in the molten polyolefin resin. Thus, in preferred embodiments, the total concentration of each blend of the at least two nucleators used in the individual polyolefin resin sample as part of determining the minimum dissolution temperature is less than 5000 ppmw, more preferably from 500 ppmw to 5000 ppmw.

In other preferred embodiments, the total concentration of each blend of the at least two nucleators in the individual polyolefin resin sample is from 1500 ppmw to 4000 ppmw; preferably 2.250 ppmw to 3250 ppmw; more preferably from 2500 ppmw to 3000 ppmw.

In other preferred embodiments, wherein the concentration of each blend of the at least two nucleators in the individual polyolefin resin sample 1500 ppmw to 2500 ppmw; preferably from 1750 ppmw to 2250 ppmw: more preferably from 1900 ppmw to 2100 ppmw.

So that a fair comparison can be made between different blends of the same at least two nucleators (i.e. where the components are present in different weight ratios in different blends), the method which is employed in determining the minimum dissolution temperature as part of the method of the present invention is the same. Any suitable method for determining the minimum dissolution temperature may thus be utilised. For example, dissolution may be determined by optical microscopy methods or conventional light scattering or differential scanning calorimetry (DSC) techniques, of which the skilled person is aware. For example, Kristiansen et al., Macromolecules, 2003, 36, 5150-5156 discusses optical microscopy and DSC techniques as relevant to assessment of dissolution/crystallization temperatures in polypropylene. The Handbook of Industrial Crystallization, Second Edition, 2002, Edited by Allan S. Myerson and published by Butterworth-Heinemann, describes light scattering methods for investigating dissolution/crystallisation. Optical microscopy and light scattering methods rely on the physicochemical changes that occur when a nucleator loses a crystalline structure at the point of dissolution, which affects the extent of light transmittance through the mixture or the extent of light scattering.

Preferably, methods for determining the minimum dissolution point do not involve the application of shear to the composition comprising the polyolefin resin and the blend of the at least two nucleators. It is also preferred if a controlled rate of heating is applied to the composition comprising the polyolefin resin and the blend of the at least two nucleators so that physico-chemical changes in the composition can be assessed more accurately as temperature is increased from below and up to the minimum dissolution temperature.

In a preferred embodiment, the minimum dissolution temperature for each blend in step ii) is determined by an optical microscopy method comprising:
  a) melt compounding each blend of the at least two nucleators with a polyolefin resin sample to form a compounded composition comprising the blend of the at least two nucleators at a concentration of at least 500 ppmw, without dissolving the blend in the polyolefin resin;
  b) raising the temperature of the composition at a controlled rate whilst continuously obtaining microscope images of the composition using a microscope with a light source configured to transmit light through the composition, a heating platform configured to heat the composition and an image capturing device configured to continuously capture microscope images of the composition, wherein the image capturing device is in communication with an analysis unit configured to determine the brightness of the captured images and brightness variability between successive captured images;
  c) determining the temperature of the composition at which a peak in relative brightness variability is observed based on analysis of the captured images and thereby obtaining the minimum dissolution temperature.

Any means for melt compounding of the blend of the at least two nucleators and the resin may be used to prepare the compounded composition for observation under the microscope. Melt compounding is effective for dispersing additives in a polyolefin resin. As the skilled person will appreciate, any workable scale quantities of resin may suitably be used to form the compounded composition. For instance, mg/g scale quantities of resin may be used to increase efficiency and reduce waste. Alternatively, for practicality, kg scale quantities of resin may be used which allow for easier measurement of ppm quantities of nucleator to be added thereto. Thus, any suitable compounder may be used depending on the scale, such as a co-/counter-twin screw batch compounder or micro-compounded (e.g. Xplore® MC-15 or Thermo Scientific® HAAKE® MiniLab II).

The resin may suitably be in flaked, granular or pelletized form, preferably pelletized form, and the blend of the at least two nucleators is suitably in powder form when mixed prior to melt compounding. Powdered nucleators which may be employed in the method of the present invention typically have fine particle sizes and, for example, have d97 values of 50 microns or less, preferably 30 microns or less, and d50 values of 25 microns or less, preferably 15 microns or less. The melt compounder is typically operated at above the softening point of the polyolefin resin, but below the minimum dissolution temperature of the blend of nucleators. Suitable temperatures at which melt compounding is conducted are from over 160° C. to less than 200° C. preferably from 175° C. to 195° C. , more preferably from 180° C. to 190° C. At these temperatures, little or no dissolution of the at least two nucleators is typically observed. Melt compounding may suitably be performed in the presence of air or an inert gas, such as nitrogen.

Once melt compounded, a compounded composition specimen may be obtained and subsequently loaded on to a heating platform, also referred to as a 'hot stage' (e.g. FP90, Mettler), coupled to a microscope (e.g. a BX41, Olympus). The compounded composition may be transferred without a cooling step or may be cooled and re-heated on the heating platform. The hot stage may be operated at a controlled heating rate (e.g. 5° C./min, 10° C./min or 15° C./min, preferably 10° C./min) for accurate measurement of physico-chemical changes during heating, in the absence of any applied shear to the compounded composition.

The microscope used in the preferred optical microscopy method is equipped with an image capturing device, such as a microscope digital camera system (e.g. Olympus DP11 or PixeLINK Microscopy Camera), so as to continuously capture images (i.e. photomicrographs/video) of the compounded composition during heating. Brightness of individual images and brightness variability between successive images may then be determined by means of an analysis unit coupled to the image capture device. The analysis unit may take the form of a computer system comprising a software package configured for processing the brightness/light transmittance data relating to the captured images (for example, PixeLINK Microscopy Software). From the brightness data, the minimum dissolution temperature may be determined based on the temperature at which maximum relative brightness variability is observed in a plot of relative brightness variability versus temperature.

The change in the physico-chemical properties of the molten composition, for instance in terms of the loss of crystallinity of the blend of at least two nucleators in the molten resin, gives rise to changes in the light transmittance through the molten composition and hence the brightness of the captured images obtained by the image capture device, Brightness variability (i.e. change in brightness between successive captured images during heating) reaches a peak upon complete dissolution of the blend of nucleators and corresponds to a maximum in relative brightness variability. Further increases in temperature after complete dissolution have little effect on brightness therefore brightness variability after dissolution of the blend of nucleators is minimal between successive captured images. This explains why the dissolution may be visualized as a peak in a plot of relative brightness variability against temperature; the temperature at which the peak in relative brightness variability is observed corresponding to the minimum dissolution temperature. This is illustrated in FIG. 1, which is a graphical representation for minimum dissolution temperature determination from the maximum value for relative brightness variability for different concentrations of 3,4-DMDBS in a molten propylene random copolymer resin (MFR 7 g/10 min).

In preferred embodiments, the method for determining the minimum dissolution temperature is repeated at least three times for each blend and the mean or median minimum dissolution temperature is determined and used as part of identification step iii). Since preparing and testing more blends in steps i) and ii) can be of benefit to the determination in step iii), the plurality of blends preferably includes at least 3, preferably at least 5, more preferably at least 10, different blends.

Once the minimum dissolution temperature has been determined for each of the plurality of blends, a blend of nucleators having a particular weight ratio of components may be identified having a minimum dissolution temperature which is lower than a majority of the plurality of blends prepared and tested in steps i) and ii). As the skilled person will appreciate, the term majority is intended to mean greater than 50% of the blends prepared and tested in steps i) and ii).

It has been consistently found that the lower the minimum dissolution temperature of a blend of nucleators, the lower the resulting haze value in the nucleated polyolefin material which is prepared therefrom. This is particularly the case where the polyolefin material is prepared by processing a polyolefin material at lower than conventional temperatures (for example, at temperatures less than 200° C.). Thus, the present invention allows for the identification of a blend of nucleators, containing the components in a particular weight ratio, which results in an advantageously low haze value in a nucleated polyolefin material prepared therefrom.

In preferred embodiments, the blend identified in step iii) corresponds to a minima in a plot of minimum dissolution temperature against weight fraction of the components of the blends, based on the minimum dissolution temperatures determined for each of the plurality of blends in step ii). As the skilled person will appreciate, by plotting a graph of the results obtained in step ii), it is possible to derive a blend having a particular weight ratio of components having the lowest minimum dissolution temperature. This may correspond to a blend of the plurality of the blends prepared and tested in steps (i) and ii). Alternatively, the blend identified in step iii) may be one that has not been prepared and tested in steps i) and ii), but is indicated (for instance, based on a plot of the results) as having a lower minimum dissolution temperature than a majority, preferably all, of the blends prepared and tested in steps i) and ii).

As the skilled person will appreciate, the data obtained in step ii) may be utilized so as to generate a "best fit" model (for example, as in the case of a non-linear regression analysis) defining the relationship of the minimum dissolution temperature and the weight fraction of the components of the plurality of blends. The skilled person will also appreciate that analytical tools and/or multiple plots may be used to identify a blend having a particular weight fraction of components, where the plurality of blends contain more than two different nucleators and the identified blend has not been prepared or tested according to steps i) and ii).

In other embodiments, the blend identified in step iii) corresponds to one or the blends of the plurality of blends prepared and tested in steps i) and ii), more preferably where the identified blend is a blend of the plurality having the lowest minimum dissolution temperature.

In preferred embodiments, there is a nonlinear relationship between the minimum dissolution temperature and the weight ratio of the nucleators in the blend. Thus, in other words, an increase in the weight fraction of one nucleator of the blend does not lead to a proportional change in the minimum dissolution temperature.

As will be appreciated by the skilled person, where data relating to different blends is utilized so as to generate a best fit or other predictive model, it is possible to identify a blend having a minimum dissolution temperature which is lower than that of the majority of the blends tested where a narrower selection of blends is tested. In particular, predictive modelling or plotting a best fit can obviate the requirement that the plurality of blends tested includes one or more blends in which one of the at least two nucleators is a major weight fraction of the blend as well as one or more blends in which the same one of the at least two nucleators is a minor weight fraction of the blend. However, this is less preferred since it is less reliable as a means for identifying a blend which is advantageous in terms of the optical properties achievable in a nucleated polyolefin material prepared therefrom at low processing temperature. Nevertheless, a narrower selection of blends in terms of the extent of weight fraction variance between the blends may still be satisfactory, particularly where a larger number of blends (for example at least 5, preferably at least 10 blends) are tested.

Thus, in accordance with the second aspect of the invention recited hereinbefore, step i) comprises preparing a plurality of blends of the at least two nucleators wherein each blend contains the same at least two nucleators but in a different weight ratio, wherein each of the plurality of blends of the at least two nucleators includes the same one nucleator as a major weight fraction of the blend.

In other preferred embodiments, the methods of the invention further comprise determining the minimum dissolution temperature for each nucleator of the plurality of blends when used individually in the polyolefin resin, wherein the total concentration of nucleator in the polyolefin resin sample used to determine the minimum dissolution temperature for each nucleator individually is substantially the same as that used for determining the minimum dissolution temperature of each of the plurality of blends, and wherein the same method for determining the minimum dissolution temperature for each of the plurality of blends is used for determining that of the nucleators of the plurality of blends individually.

It has been found that the methods of the present invention are suitable for identifying synergistic effects between the components of the blends as far as minimum dissolution temperature and corresponding haze values are concerned. Where the blend identified in step iii) has a minimum dissolution temperature which is lower than all of the components of the blend individually, this indicates that the effect of blending the components is not merely additive but indicates that there is some form of synergy which gives rise to a lower minimum dissolution temperature and hence a lower haze values.

Any suitable nucleator may be used which is capable of nucleating a polyolefin and has solubility in polyolefin. In preferred embodiments, the blends of the at least two nucleators contain two or three different nucleators only. More preferably, the blends of the at least two nucleators contain two different nucleators only. In a particularly preferred embodiment, the blends contain two nucleators only and the plurality of blends includes blends having weight ratios evenly distributed across an individual nucleator concentration range of above 0 wt % to below 100 wt. %.

In preferred embodiments, the nucleators of the blends are selected from substituted dibenzylidene sorbitol derivatives; 1,3,5-benzenetrisamides; trans- or dimethyl-quinacridone; and N,N'-di-C5-C8-cycloalkyl-2,6-naphthalene dicarboxamides. More preferably, the nucleators of the blends are selected from substituted dibenzylidene sorbitol derivatives and 1,3,5-benzenetrisamides. Most preferably, the nucleators of the blends are selected from substituted dibenzylidene sorbitol derivatives.

The substituted dibenzylidene sorbitol derivatives are preferably selected from those according to Formula I below:

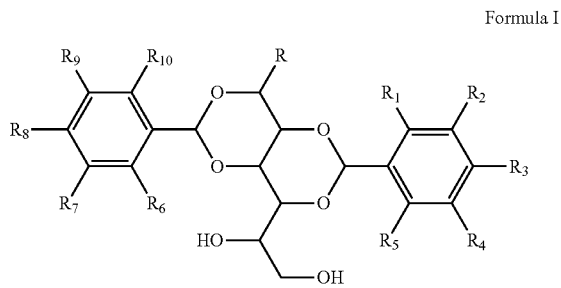

Formula I wherein $R_1$, $R_2$, $R_3$, $R_4$, $R_5$, $R_6$, $R_7$, $R_8$, $R_9$, $R_{10}$ are the same or different and are selected from hydrogen, $C_1$ to $C_6$ alkyl, $C_1$ to $C_4$ alkoxy, $C_1$ to $C_4$ alkoxycarbonyl, halogen, hydroxy, $C_1$ to $C_6$ alkylthio, $C_1$ to $C_6$ alkylsulfoxy, provided that at least one of $R_1$ to $R_{10}$ is other than hydrogen; and R is selected from hydrogen, $C_1$ to $C_8$ alkyl, $C_2$ to $C_8$ alkenyl, $C_1$ to $C_8$ alkoxy, $C_1$ to $C_8$ alkylhydroxy, and $C_1$ to $C_8$ haloalkyl. Preferably, $R_1$, $R_2$, $R_3$, $R_4$, $R_5$, $R_6$, $R_7$, $R_8$, $R_9$, $R_{10}$ are the same or different and are selected from hydrogen, $C_1$ to $C_4$ alkyl, chlorine and bromine provided that at least one of $R_1$ to $R_{10}$ is other than hydrogen; and R is selected from hydrogen and $C_1$ to $C_4$ alkyl. In particularly preferred embodiments, R is hydrogen.

Examples of preferred substituted dibenzylidene sorbitol derivatives include bis-p-methylbenzylidene sorbitol, di(p-chlorobenzylidene) sorbitol, di(o-methylbenzylidene) sorbitol, bis-p-ethylbenzylidene sorbitol, bis(3,4-dimethylbenzylidene) sorbitol, and bis(3,4-diethylbenzylidene) sorbitol, and bis(4-propylbenzylidene) propylsorbitol. More preferably, the substituted dibenzylidene sorbitol derivatives are selected from bis(3,4-dimethylbenzylidene) sorbitol, bis-p-ethylbenzylidene sorbitol and bis-p-methylbenzylidene sorbitol; most preferably wherein the substituted dibenzylidene sorbitol derivatives are selected from bis-p-ethylbenzylidene sorbitol and bis-p-methylbenzylidene sorbitol.

In some embodiments, the blend of the at least two nucleators does not include the combination of bis(3,4-dimethylbenzylidene) sorbitol and bis-p-ethylbenzylidene sorbitol.

The 1,3,5-benzenetrisamides are preferably selected from N-[3,5-Bis-(2,2-dimethylpropionylamino)-phenyl]-2,2-dimethylpropionamide and N,N',N"-Tris(2-methylcyclohexyl) 1,2,3-propanetricarboxamide.

The N,N'-di-$C_5$-$C_8$-cycloalkyl-2,6-naphthalene dicarboxamide is preferably selected from N,N'-dicyclohexyl-2,6-naphthalene dicarboxamide and N,N'-dicyclooctyl-2,6-naphthalene dicarboxamide.

In particularly preferred embodiments, at least one of the nucleators in the blends is also a clarifier, preferably wherein all of the nucleators of the blends are also clarifiers.

In preferred embodiments, the methods of the invention further comprise a step iv) of preparing a nucleated polyolefin material using the blend identified in step iii) by preparing a polyolefin resin composition comprising the at least two nucleators in the weight ratio according to the blend identified in step iii) and processing said polyolefin resin composition to form said polyolefin material.

Reference herein to a "polyolefin resin composition" is intended to refer to a polyolefin resin in which the blend of the at least two nucleators has been dissolved. Thus, preparation of a polyolefin resin composition may comprise dissolving the blend of the at least two nucleators in a molten polyolefin resin at a specific weight ratio.

Reference herein to a "polyolefin material" is intended to refer to any thermoplastic article or object which may suitably be prepared from processing a molten polyolefin resin composition, as described hereinbelow. Following processing, the formed polyolefin material is no longer molten, but a semi-crystalline solid, with a highly ordered molecular structure. The blend of nucleators dissolved in the polyolefin resin composition form crystals upon cooling after processing, typically forming a three dimensional network of dispersed crystals which act as nucleation sites facilitating crystallization of the polyolefin upon formation of the polyolefin material.

Where reference is made herein to processing the polyolefin resin composition in order to form the nucleated polyolefin material, this may be by any suitable means of which the skilled person is aware. Suitably, any of the conventional moulding methods can be employed to mould the resin composition of the invention. Illustrative of such moulding methods are injection moulding, injection stretch moulding, extrusion moulding, blow moulding, vacuum moulding, rotational moulding and film moulding. Thus, for example, the polyolefin resin composition may first be prepared by blending the crystalline resin directly with the blend of nucleators identified in step iii) in the specific weight ratio, before the resulting mixture is moulded into the desired product. Alternatively, the blend of nucleators may be incorporated into the resin before pelletizing the mixture, and thereafter moulding the same into the polyolefin material.

Processing of the polyolefin resin composition preferably comprises injection and/or extrusion moulding the polyolefin resin composition. It has been found to be particularly beneficial to the performance of the blend of at least two nucleators in conferring desirable optical properties to the nucleated polyolefin material if the blend of nucleators is melt compounded with the polyolefin resin and extruded before the resulting polyolefin resin composition is processed to form the polyolefin material. Melt compounding is believed to give rise to better dispersion of the nucleators in the resin and the inventors have found that optical properties in the polyolefin material, particularly haze value is improved as a result, in comparison to simply mixing the components of the resin composition and moulding only.

Thus, in preferred embodiments, there is an intermediate step of melt compounding and extruding the components of the polyolefin resin composition prior to processing to form the polyolefin material. In particularly preferred embodiments, where a nucleated polyolefin material is prepared in step iv) using a blend identified in step iii) there is an intermediate step of melt compounding and extruding the components of the polyolefin resin composition before the resulting polyolefin resin composition is injection moulded to form the polyolefin material in step iv).

As described hereinbefore, it is possible by means of the present invention to identify blends of nucleators exhibiting relatively low minimum dissolution temperatures in a polyolefin resin. Furthermore, it has also been possible to identify blends which exhibit a surprising synergy, where minimum dissolution temperature is low for the blend of nucleators than any of the nucleators individually. Similarly, where there is a nonlinear relationship between minimum dissolution temperature and weight fraction of the components of the blend, it is possible to identify a blend of nucleators having a particular weight fraction that has an unexpectedly low minimum dissolution temperature having regard to the minimum dissolution temperatures of components of the blends individually. As a result, the processing temperature over which a nucleated polyolefin material exhibiting low haze may be effectively prepared may be broadened considerably so as to cover temperatures much lower than those which would normally be feasible.

Preferably, processing of the polyolefin resin composition to form said polyolefin material is conducted at a temperature of from 180° C. to 245° C., preferably from 185° C. to 230° C. Other preferred processing temperature ranges used in the preparation of the polyolefin material include: 200° C. or below, for example from 180° C. to 200° C., more preferably from 185° C. to 198° C., even more preferably at a temperature of from 190° C. to 197° C., most preferably from 190° C. to 195° C.

Reference herein to the "temperature at which processing of the resin composition is conducted" or the "processing temperature" is intended to refer to the temperature at which the molten polyolefin composition is processed in order to prepare the polyolefin material. Thus, the processing temperature includes the mould temperature (e.g. injection or extrusion moulding) of the molten polyolefin composition. As will be appreciated, higher temperatures may be employed to ensure dispersion and dissolution of the combination of nucleators in the polyolefin resin than are subsequently employed for processing (i.e. moulding) the resulting polyolefin composition. For instance, complete dissolution of the blend of nucleators in the molten polyolefin resin may be achieved at or above the minimum dissolution temperature of the particular combination of nucleators in the resin. However, in at least some embodiments, the processing temperatures used for moulding the polyolefin composition may be lower than the minimum dissolution temperature of the blend of nucleators in the resin, without there being plate-out or precipitation of nucleators so as to preclude a positive effect on haze properties. It will also be appreciated that satisfactory dispersion and dissolution of the blend of nucleators may also be achieved in the resin at temperatures lower than the minimum dissolution temperature of the blend in a particular resin, particularly when shear is applied to the mixture.

Reference herein to "haze value" is intended to refer to the amount of transmitted light that is scattered upon passing through a film or sheet of material. Haze values reported herein were determined following ASTM method D1003-61 ("Standard Test Method for Haze and Luminous Transmittance of Transparent Plastics") and are quoted together with the specific plaque thickness (e.g. 0.5 mm or 1 mm) of the test material, the temperature under which the polyolefin resin is injection moulded (e.g. 180° C., 100° C. or 200° C.), and the total content of nucleator in the resin. Haze may be measured using, for instance, a haze meter such as BYK Gardner Haze Guard Plus.

In some embodiments, the blend identified in step iii), when used to prepare a nucleated polyolefin material, provides a polyolefin material with a lower haze value, as measured in accordance with ASTM D1003-61 for a 1 mm thick plaque, compared to a nucleated polyolefin material prepared from any of the nucleators of the blend used individually, when substantially the same total nucleator concentration is used in preparing the polyolefin materials. Preferably, a lower haze value is achieved when the nucleated polyolefin material is prepared in each case by processing a polyolefin resin composition at temperatures of less than 200° C.

Preferably, the nucleated polyolefin material which may be prepared in accordance with step iv) of the present invention has a haze value, as measured in accordance with ASTM D1003-61 for a 2 mm thick plaque, of below 45%, more preferably below 42%, still more preferably below 40%, most preferably below 38%, for example 37%, or 36%. Preferably, these levels of haze are obtained by processing the polyolefin resin composition at temperatures below 200° C., for example from 185° C. to 198° C., more preferably at a temperature of from 190° C. to 197° C., most preferably from 190° C. to 195° C.

Preferably, the nucleated polyolefin material which may be prepared in accordance with step iv) of the present invention has a haze value, as measured in accordance with ASTM D1003-61 for a 1 mm thick plaque, of below 20%, more preferably below 15%, still more preferably below 13%, most preferably below 12%, for example 11%, or 10%. Preferably, these levels of haze are obtained by processing the polyolefin resin composition at temperatures below 200° C., for example from 180° C. to 200° C., preferably from 185 ° C. to 198° C., even more preferably at a temperature of from 190° C. to 197° C., most preferably from 190° C. to 195° C.

Preferably, the nucleated polyolefin material which may be prepared in accordance with step iv) of the present invention has a haze value, as measured in accordance with ASTM D1003-61 for a 0.5 mm thick plaque, of below 15%, more preferably below 10%, still more preferably below 8%, most preferably below 6%, for example 5%, or 4%. Preferably, these levels of haze are obtained by processing the polyolefin resin composition at temperatures below 200° C., for example from 180° C. to 200° C., preferably from 185° C. to 198° C., even more preferably at a temperature of from 190° C. to 197° C., most preferably from 190° C. to 195° C.

The polyolefin resin used in accordance with the present invention refers to any stereoregular, crystalline resin which may suitably be used for preparing a polyolefin material, particularly one having low haze. Examples of suitable polyolefin resins include polyethylene resins, polypropylene resins, polybutylene resins, or blends or copolymers thereof. Preferably, the polyolefin resin is selected from polypropylene resins.

There is no specific restriction on the production method, type of stereoregularity, crystallinity, type, components of a blend, or the molecular weight distribution of the polyolefin resins. Examples of the polyethylene resins include high-density polyethylene, medium-density polyethylene, low-density polyethylene, linear low-density polyethylene and ethylene copolymers with an ethylene content of 50 wt. % or more. Examples of polypropylene resins include isotactic or syndiotactic propylene homopolymers and propylene copolymers with a propylene content of 50 wt. % or more. Examples of polybutene resins include isotactic or syndiotactic butane homopolymers and butane copolymers with a butane content of 50 wt. % or more.

The above copolymers may be random copolymers ("RACO"), homo- or block-copolymers. For example, the polyolefin resin may be a polypropylene random compolymer (RACO).

Comonomers which can form the above copolymers are, for example, $C_2$-$C_{16}$ alpha-olefins such as ethylene, propylene, butane, pentane, hexene, heptene, octane, nonene, decene, undecene and dodecene; acrylic or methacrylic acid esters, particularly $C_1$-$C_{18}$ alkyl esters, such as methyl acrylate, methyl methacrylate, ethyl acrylate, ethyl methacrylate, butyl acrylate, butyl methacrylate, octyl acrylate, octyl methacrylate, stearyl acrylate, stearyl methacrylate and the like: vinyl acetate; 1,4-endomethylenecyclohexene and like bicyclo monomers.

Catalysts useful for the production of the polymers include not only radical polymerization catalysts and Ziegler-Natta catalysts which are commonly employed in the art, but also catalyst systems comprising a catalyst prepared by depositing a transition metal compound (e.g., titanium halide such as titanium trichloride or titanium tetrachloride) on a support mainly composed of magnesium chloride or like magnesium halide, in combination with an alkyl aluminum compound (such as triethyl aluminum or diethyl aluminum chloride) and; said catalyst systems further comprising a specific ester compound and an organic ether compound; metallocene catalysts comprising a cyclopentadiene or its derivative and a metal of the fourth group such as titanium or zirconium; and said "metallocene catalysts" further comprising methylalumoxane.

The melt flow rate (MFR) of the polyolefin-based resin for use in the invention, measured according to ASTM method D1238-04, may be suitably selected according to the moulding method to be employed and physical properties required of the moulded article. Typically, the MFR for a polyolefin resin suitably varies from 0.01 to 200 g/10 min, preferably from 0.05 to 100 g/10 min. In other preferred embodiments,: the MFR value of the polyolefin resin used in accordance with the present invention is 5 g/10 min or above. Polyolefin resins having higher MFRs are more compatible with lower processing temperatures. Thus, in other preferred embodiments, the MFR of the polyolefin resin may be 20 g/10 min or above. In other preferred embodiments, the MFR of the polyolefin resin may be 40 g/10 min or above, for example 50 g/10 min. In other preferred embodiments, the MFR of the polyolefin resin may be 70 g/10 min or above, for example 80 g/10 min. The molecular weight distribution (Mw/Mn) of the resin is not limited, but is usually from 1 to 10.

It is known that polyolefin resins having higher MFR values, i.e. lower viscosities, can typically be processed at lower temperature. Thus, using the blend of nucleators identified in accordance with the present invention, together with polyolefin resins having higher MFR values, for instance 20 g/10 min or above, may be particularly advantageous for preparing a polyolefin material having desirably low haze at lower than conventional processing temperature (e.g. below 200° C.).

The polyolefin resin may be a multimodal, or bimodal or unimodal composition, where modality of the polymer refers to the form of its molecular weight distribution curve (i.e. molecular weight fraction as a function of its molecular weight). For instance, polymer components may be produced in a sequential step process, using reactors arranged in series operating under different reaction conditions. Consequently, each fraction prepared in a specific reactor will have its own molecular weight distribution. When such fractions are combined, it is possible that the molecular weight distribution curve of the final polymer displays multiple maxima, or may be substantially broadened in comparison to the molecular weight distribution curves for the individual fractions.

Furthermore, where necessary, rigidity-imparting nucleating agents or fillers can also be added to the polyolefin resin in an amount which does not compromise the effects of the present invention (e.g., up to about 50 wt. parts, in particular about 0.01 to 20 wt. parts, per 100 wt. parts of the polyolefin resin). For instance, talc, hydrotalcite, mica, zeolite, perlite, diatomaceous earth, calcium carbonate and aluminum hydroxy-bis-tert-butylbenzoate may be added to the polyolefin resin.

The polyolefin resin for use in the present invention may contain other additives such as stabilizers, neutralizing agents, antistatic agents, lubricants and one or more optical brighteners. These known additives may be used in combination, insofar as they do not compromise the effects of the invention.

Optical brighteners, also known as fluorescent whitening agents (FWA), are known to absorb ultraviolet light energy and re-emit light by fluorescence mostly in the blue region of the visible spectrum, at a wavelength of approximately 400 to 500 nm. Optical brighteners can be used to reduce the appearance of yellow in materials resulting from a "blue deficit" in the light reflected therefrom.

Any suitable optical brightener may be used in connection with the present invention, such as those which are known for use in improving optical properties of polyolefin materials and having sufficient thermal stability for extrusion or injection moulding processes associated with the preparation of polyolefin materials. Examples of suitable classes of the one or more optical brighteners for use in the present invention include bis-benzoxazoles, phenylcoumarins, methylcoumarins, bis-(styryl)biphenyls, and combinations thereof, which are, for example, described in detail in *Plastics Additives Handbook*, Hanser Gardner Publications, 6th Edition, H. Zweifel, D. Maier, M. Schiller Editors, 2009.

Particularly preferred examples of optical brighteners are selected from the bis-benzoxazole class, namely 2,5-bis(5-tert-butyl-benzoxazol-2-yl)thiophene and 4,4'-bis-benzoxazolyl-stilbene, which are discussed in detail in: *Plastics, Additives and Compounding*, Volume 5, Issue 6, June 2003. 4,4'-bis-benzoxazolyl-stilbene, (CAS #: 1533-45-5), complies with regulations for indirect food additives administered by the U.S. Food and Drug Administration at 21 CFR 178.3297 (Colorants for Polymers). 4,4'-bis-benzoxazolyl-stilbene is also listed in European Union Directive 2002/72/EC as PM/Ref. No. 38515 for use in plastics for indirect food contact. 2,5-bis(5-tert-butyl-benzoxazol-2-yl)thiophene (CAS #: 7128-64-5): is listed in European Union Directive 2002/72/EC as PM/Ref No. 38560 for use in plastics for indirect food contact.

Specific examples of commercially available bis-benzoxazole optical brighteners include: Tinopal® family from BASF, which such as Tinopal AEF A, Tinopal ABP-X, Tinopal ASP, Tinopal BPO, TinopalEC, Tinopal HST. Tinopal Tinopal MSP, Tinopal NP, Tinopal SPP N, Tinopal SPP-Z, Tinopal UP HC DD, Tinopal UP, Tinopal CBS-X and Tinopal® OB; UVITEX® compounds from Ciba Specialty Chemicals, such as UVITEX® OB, UVITEX® OB-C, UVITEX® OB-P, UVITEX® FP, UVITEX® FP-C; Eastobrite® compounds from Eastman Chemical, such as Eastobrite® OB, Eastobrite® OB-1 and Eastobrite® OB-3, Hostalux® compounds from Clariant, such as Hostalux ACK, Hostalux CP01, Hostalux EBU, Hostalux EF, Hostalux ERE, Hostalux EREN, Hostalux ES2R, Hostalux ESR, Hostalux ETB 300, Hostalux ETBN, Hostalux KCB, Hostalux KS, Hostalux KS1 B, Hostalux KSB3, Hostalux KSC, Hostalux KSN, Hostalux NR, Hostalux NSM, Hostalux PFC, Hostalux PFCB, Hostalux PN, Hostalux PNB, and Hostalux PR, Whitefluor® compounds (bis-(styryl)-benzoxazoles) from Sumitomo Chemical Co,, such as Whitefluor® B, Whitefluor® PEN, Whitefluor® PHP, Whitefluor® HCS, Whitefluor® PCS, Specific examples of phenylcourriarins and methylcoumarins include 3-phenyl-7-(4-methyl-6-butyloxybenzoxazole)coumarin and 4-methyl-7-diethylamincoumarin, respectively.

Specific examples of commercially available methylcoumarin optical brighteners are Eccowhite® compounds from Eastern Color & Chemical Co., such as Eccowhite 1 132 MOD, Eccowhite 2013, Eccowhite 2790, Eccowhite 5261, Eccowhite AEA-HF, Eccowhite Nylon FW, Eccowhite OP, Eccowhite PSO, Eccowhite DM-04 MOD.

One or more optical brighteners may be used at a level which leads to an improvement in optical properties (for instance, a yellowness reduction) in the polyolefin material which is prepared. Preferably, a minimum amount of the one or more optical brighteners is used which is sufficient for achieving the desired benefit to optical properties of the polyolefin material.

In some embodiments, the total amount of the one or more optical brighteners in the polyolefin resin composition is from 1 to 100 ppm, by weight of the polyolefin resin composition, preferably from 2 to 50 ppm, and more preferably from 5 to 20 ppm, by weight of the polyolefin resin composition.

Preferably, the nucleated polyolefin material which may be prepared in accordance with step iv) of the present invention has a Yellowness Index (YI), as measured in accordance with ASTM E313 for a 2mm thick plaque, of less than 7.5, more preferably less than 5, even more preferably less than 2.5, most preferably less than 0.5.

Preferably, these levels of Yellowness index are obtained by processing the polyolefin resin composition at temperatures below 200° C., for example from 180° C. to 200° C., preferably from 185° C. to 198° C. even more preferably at a temperature of from 190° C. to 197° C., most preferably from 190° C. to 195° C.

In addition to the blend of nucleators which is soluble in the molten polyolefin resin composition, additional non-soluble nucleators may be included in the polyolefin resin composition, provide they do not interfere with or otherwise diminish the effects of the blend of nucleators identified in step (iii) of the methods of the invention in the polyolefin material. For instance, the polyolefin resin composition may additionally comprise non-soluble nucleators such as bisphenol phosphates, metal salts of rosin acids, sodium and aluminium salts of benzoic acid and p-t-butylbenzoic acid, alkali metal and alkaline earth metal salts of bicyclo[2.2.1]heptane dicarboxylic acid and 1,2-cyclohexane dicarboxylic acid, alkaline earth metal salts of glutaric, pimelic and suberic acids.

Any suitable means for admixing the blend of nucleators, any optional additives and the polyolefin resin of which the skilled person is aware may be used for forming the polylefin resin composition. The method for addition of the blend of nucleators to the polyolefin resin in order to form a polyolefin resin composition is thus not specifically limited, although it is preferable to use a single-stage addition method wherein the blend of nucleators are added to the resin directly, at the required ratio. However, a two-stage addition method can also be employed, wherein the nucleators are added in the form of a masterbatch having a concentration of about 2 to about 15% by weight, provided the batch contains the agents in the required ratio. Dissolution of the nucleators in a polyolefin resin composition may be enhanced by increasing the levels of shear during resin processing.

In another aspect, the present also provides a nucleated polyolefin material obtainable by a method which includes step iv) as described herein.

In yet another aspect, the present invention also provides an optical microscopy method for determining a minimum dissolution temperature of a nucleator, or a blend of more than one nucleator, in a molten polyolefin resin, wherein the minimum dissolution temperature is the minimum temperature at which a given concentration of a nucleator, or a blend of more than one nucleator, becomes completely dissolved in a molten polyolefin resin composition, in the absence of any applied shear, said method comprising:

a) melt compounding a nucleator, or a blend of more than one nucleator, with a polyolefin resin sample to form a compounded composition comprising the nucleator, or a blend of more than one nucleator, at a concentration of at least 500 ppmw, without dissolving the nucleator in the polyolefin resin;

b) raising the temperature of the composition at a controlled rate whilst continuously obtaining microscope images of the composition using a microscope with a light source configured to transmit light through the composition, a heating platform configured to heat the composition and an image capturing device configured to continuously capture microscope images of the composition, wherein the image capturing device is in communication with an analysis unit configured to determine the brightness of the captured images and brightness variability between successive captured images;

c) determining the temperature of the composition at which a peak in relative brightness variability is observed based on analysis of the captured images and thereby obtaining the minimum dissolution temperature.

As will be appreciated, compatible embodiments described hereinbefore relating to the determination of the minimum dissolution temperature also apply to the above method. Thus, for example, the amount of nucleator, or a blend of more than one nucleator, in the compounded composition in the above method is from 500 ppmw to 5000 ppmw.

In other preferred embodiments, the concentration of the nucleator, or a blend of more than one nucleator, in the compounded composition is from 1500 ppmw to 4000 ppmw; preferably 2250 ppmw to 3250 ppmw; more preferably from 2500 ppmw to 3000 ppmw.

In other preferred embodiments, the concentration of the nucleator, or a blend of more than one nucleator, in the compounded composition is from 1500 ppmw to 2500 ppmw; preferably from 1750 ppmw to 2250 ppmw; more preferably from 1900 ppmw to 2100 ppmw.

Figure 2:
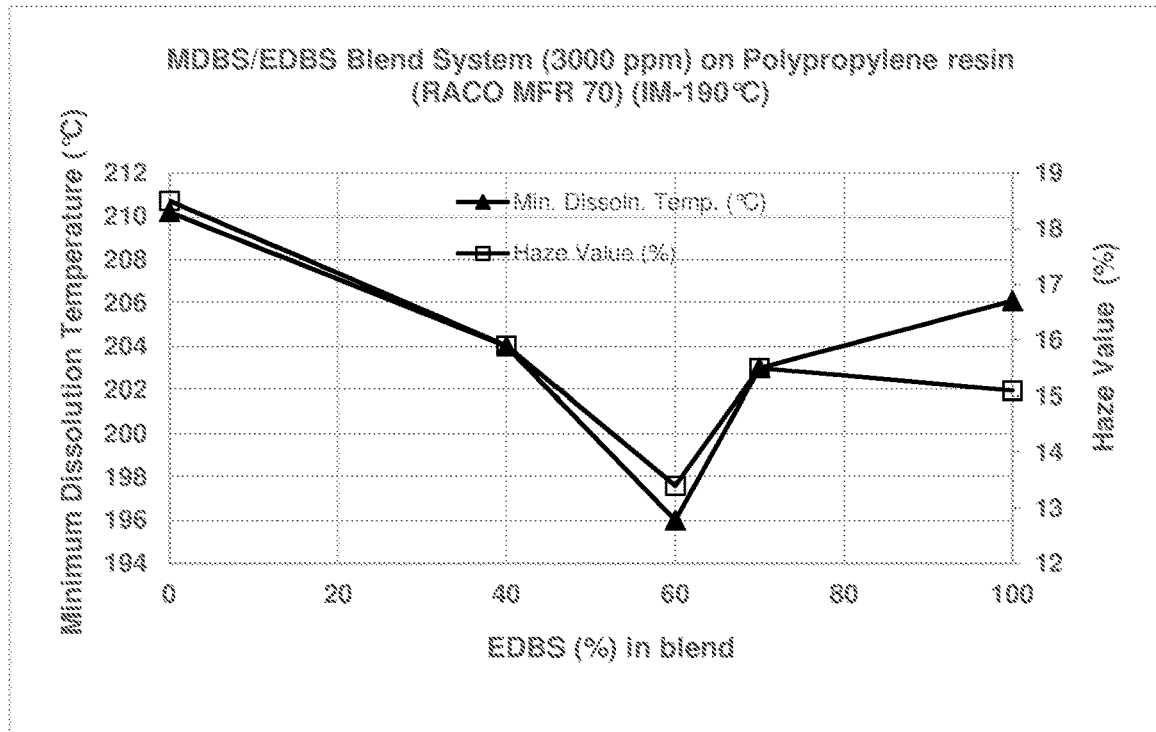
Figure 3:
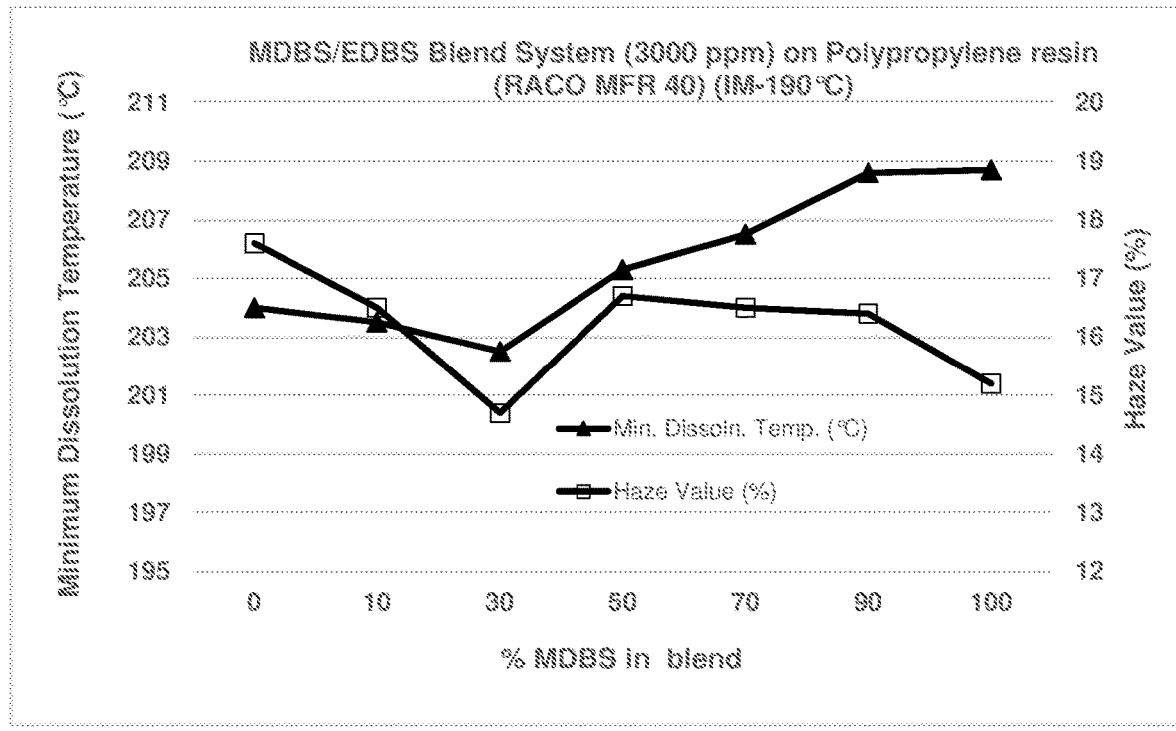
Figure 4:
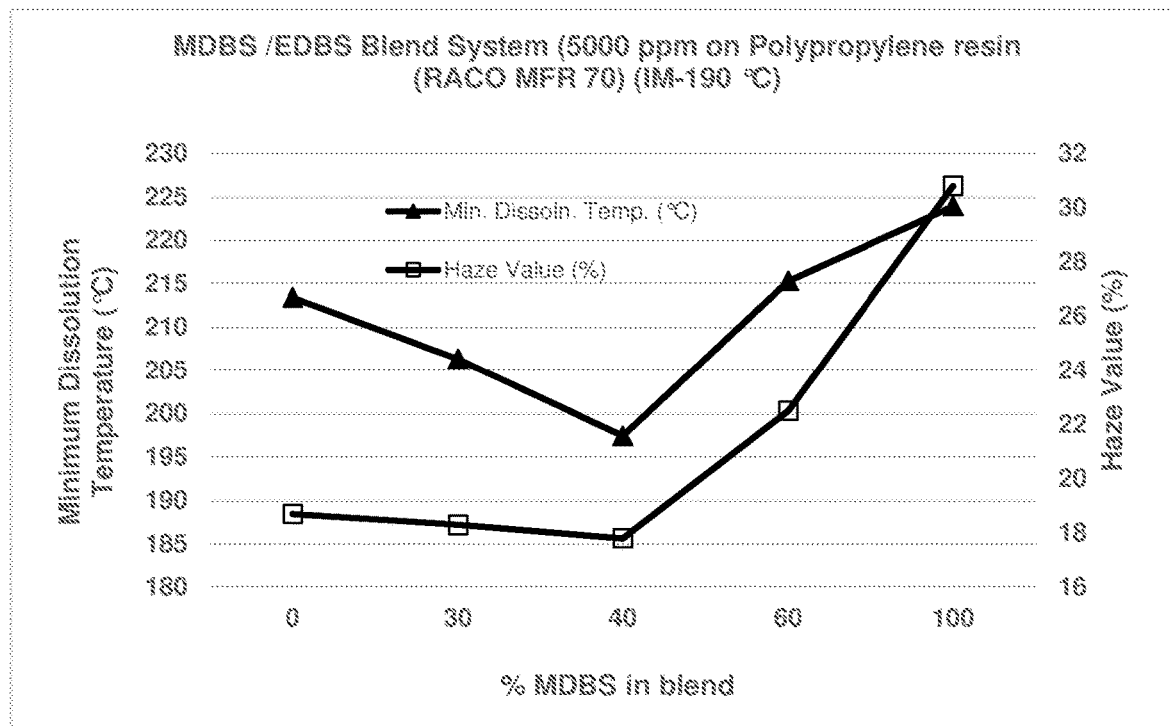
Figure 5:
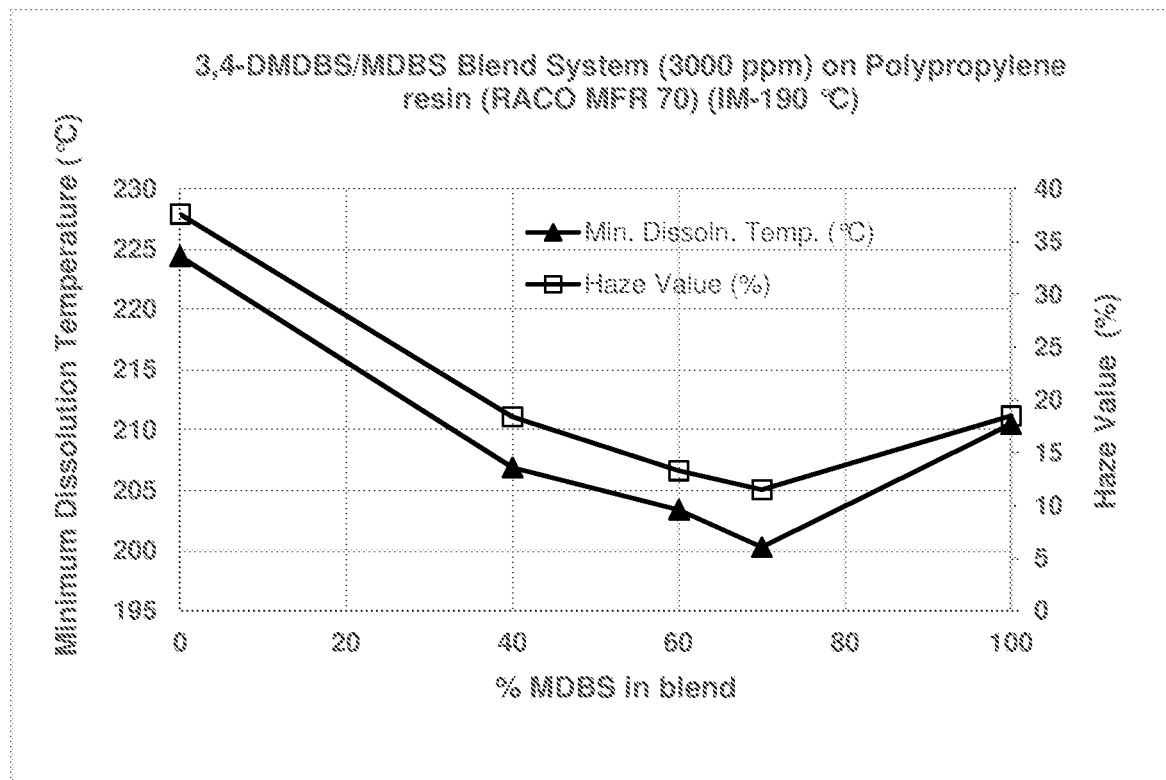
Figure 6:
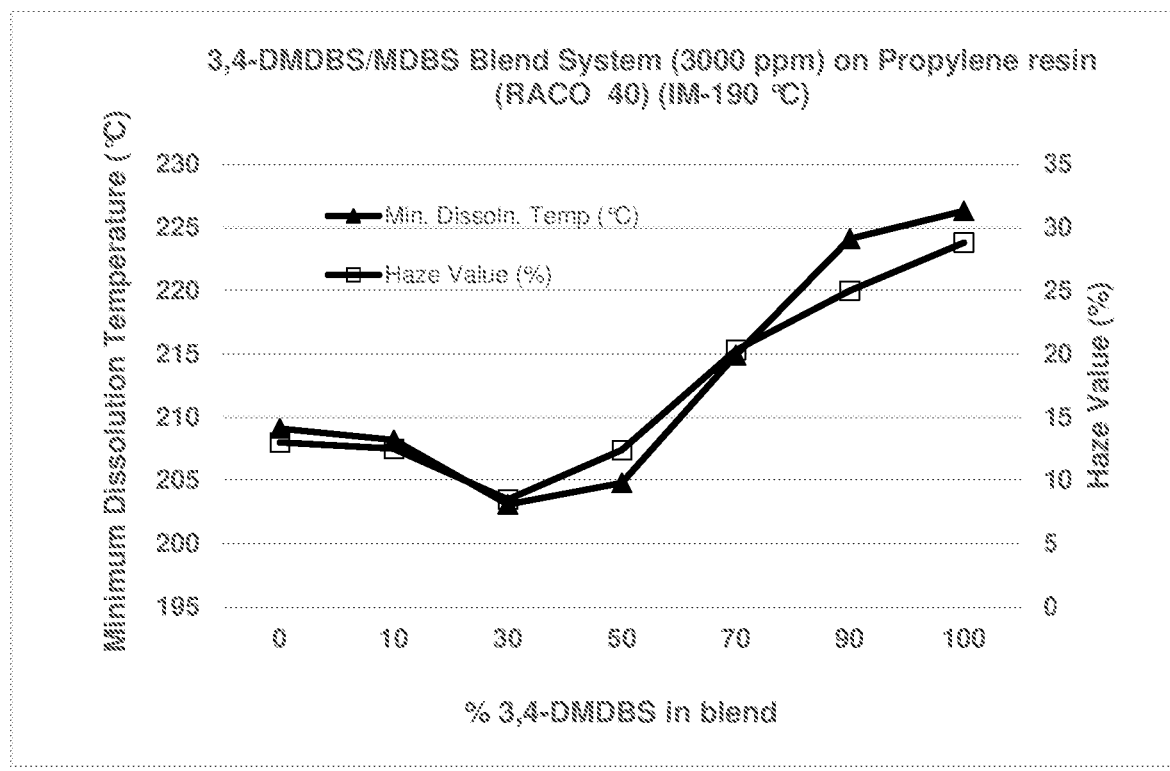

The present invention will now be illustrated by way of the following examples and with reference to the following figures:

FIG. 1: Graphical representation for minimum dissolution temperature determination from the maximum value for relative brightness variability for different concentrations of 3,4-DMDBS in a molten propylene random copolymer resin (MFR 7 g/10 min);

FIG. 2: Graphical representation of minimum dissolution temperature (° C.) for various blends of MDBS and EDBS in molten propylene random copolymer resin (MFR 70 g/10 min), at a combined concentration of 3000 ppm, based on the total weight of the resin composition, as well as haze values for a polyolefin material prepared by injection moulding the corresponding resin composition at 190° C. ("IM-190° C.");

FIG. 3: Graphical representation of minimum dissolution temperature (° C.) far various blends of MDBS and EDBS in molten propylene random copolymer resin (MFR 40 g/10 min), at a combined concentration of 3000 ppm, based on the total weight of the resin composition, as well as haze values for a polyolefin material prepared by injection moulding the corresponding resin composition at 190° C. ("IM-190° C.");

FIG. 4: Graphical representation of minimum dissolution temperature (° C.) for various blends of MDBS and EDBS in molten propylene random copolymer resin (MFR 70 g/10 min), at a combined concentration of 5000 ppm, based on the total weight of the resin composition, as well as haze values for a polyolefin material prepared by injection moulding the corresponding resin composition at 190° C. ("IM-190° C.");

FIG. 5: Graphical representation of minimum dissolution temperature (° C.) for various blends of 3,4-DMDBS and MDBS in molten propylene random copolymer resin (MFR 70 g/10 min), at a combined concentration of 3000 ppm, based on the total weight of the resin composition, as well as haze values for a polyolefin material prepared by injection moulding the corresponding resin composition at 190° C. ("IM-190° C.");

FIG. 6: Graphical representation of minimum dissolution temperature (° C.) for various blends of 3,4-DMDBS and MDBS in molten propylene random copolymer resin (MFR 40 g/10 min), at a combined concentration of 3000 ppm, based on the total weight of the resin composition, as well as haze values for a polyolefin material prepared by injection moulding the corresponding resin composition at 190° C. ("IM-190° C."); and FIG. 7: Graphical representation of minimum dissolution temperature (° C.) for various blends of 3,4-DMDBS and EDBS in molten propylene random copolymer resin (MFR 70 g/10 min), at a combined concentration of 3000 ppm, based on the total weight of the resin composition, as well as haze values for a polyolefin material prepared by injection moulding the corresponding resin composition at 190° C. ("IM-190° C.").

EXAMPLES

Minimum Dissolution Temperature

The minimum dissolution temperature (° C.) in the examples was measured using compounded pelletized samples of base resin (described in further detail below). The particular compounded pellets were melt compounded at 190° C. in the presence of air, thereby avoiding complete dissolution of the nucleators tested, The nucleator containing pellets were melted above the polyolefin's softening point (>160° C.) at a rate of 10° C./min up to 230° C. As the temperature increased, the nucleator dispersion eventually dissolved completely into the molten resin and the temperature was recorded over the course of the phase change. Molten pellets were observed using a microscope (BX41, Olympus) with hot stage (FP90, Mettler) and microscope digital camera system (PixeLINK Microscopy Camera).

Changes in light transmittance/brightness were recorded by the camera system and analysed by means of a computer software program (PixeLINK Microscopy Software—Capture Standard Edition). From the light transmittance/brightness data, the minimum dissolution temperature was determined based on the temperature at which maximum relative brightness variability was observed in a plot of relative brightness variability versus temperature.

FIG. 1 corresponds to the plot observed when determining the minimum dissolution temperature according to the above general method for different concentrations (1000, 2000, 3000 and 4000 ppm) of 3,4-DMDBS in molten polypropylene "RACO" MFR 7 g/10 min. Maximum values for relative brightness variability and minimum dissolution temperature in each case are shown to increase as the concentration of 3,4-DMDBS in the molten resin composition increases.

Haze Value

The haze value of the polyolefin material formed was measured according to ASTM Standard Test Method D1003-61 "Standard Test Method for Haze and Luminous Transmittance of Transparent Plastics" using a Gardner Hazegard Plus.

General Procedure for Preparation of Polyolefin Material

The base resin (1 kg) (random copolymer, hereinafter "RACO") and all additives were weighed and then blended in a Super mixer for 2 minutes at 1500 rpm. All samples were then melt compounded on a twin screw extruder at a ramped temperature from about 170° C. to 185° C.. The melt temperature upon exit of the extruder die was about 190° C., After a period of cooling, pelletized samples were subsequently used for minimum dissolution temperature measurements. Plaques of the target polyolefin material were then made on 25 ton injection moulder using the pelletized samples. The moulder barrel was set at the specific temperature indicated below, Plaques were prepared having dimensions of 75 mm×75 mm×Z mm, where thickness, Z, is 0.5. mm, 1 mm or 2 mm, using a mirror-polished mould. Cooling circulating water in the mould was controlled at a temperature of 20° C.. Once prepared, the plaques were rested for 24 hours at room temperature before being analysed to determine their respective Haze values.

The polyolefin base resin used in the present examples was a polypropylene of the following composition:

| | |
|---|---|
| Polypropylene random copolymer powder | 1000 g |
| Irganox ® 1010, Primary Antioxidant (from BASF) | 500 ppm |
| Irgafos ® 168, Secondary Antioxidant (from BASF) | 500 ppm |
| Calcium Stearate, Acid Scavenger | 500 ppm |
| Nucleators or blends thereof | (as indicated below) |

Blends of nucleators were prepared by admixing the components in powder form at the desired ratio, before being blended with the base resin as described above.

3,4-DMDBS and MDBS used in the examples were obtained from New japan Chemical (Geniset® DXR and Geniset® MD, respectively). EDBS was prepared in accordance with the following method. A 5 L reaction kettle, equipped with a stirrer and nitrogen inlet, was charged with 400 g of sorbitol in 2400 g of methanol. 416 g of ethylbenzaldehyde and a catalyst methanol solution (6 g of p-toluenesulfonic acid in 100 g of methanol) were added to the reaction vessel. The solution was stirred at 50° C. for 24 hours, during which time a white precipitate formed, which was isolated by filtration and washed with methanol to give a white powder. The powder was suspended at pH 8 with a small amount of KOH, and the suspension heated to boiling point, then filtered. The white powder obtained was washed with boiling water and further neutralized to pH 7. The suspension was heated to boiling point before being filtered. The precipitated white powder obtained was rinsed with methanol before a further filtration afforded a white solid. The isolated white powder was dried in a vacuum oven at 80° C. to give 370 g of EDBS product having a purity above 99% (58% yield).

Example 1

The minimum dissolution temperatures of MDBS, EDBS and blends thereof at a concentration of 3000 ppm in molten polypropylene "RACO" MFR 70 g/10 min were determined followed by determination of haze values for polypropylene materials prepared therefrom in accordance with the general procedure described above. The results are provided in Table 1 below.

TABLE 1

| MDBS (ppm) | EDBS (ppm) | MDBS: EDBS ratio | Min. Dissoln. Temp. (° C.) | Haze (ASTM-D1003-61 - 1 mm) | | |
|---|---|---|---|---|---|---|
| | | | | IM-180° C. | IM-190° C. | IM-200° C. |
| 0 | 3000 | 0:100 | 206 | 17.8 | 15.1 | 15.1 |
| 3000 | 0 | 100:0 | 210 | 21.8 | 18.5 | 18.5 |
| 900 | 2100 | 30:70 | 203 | 15.6 | 15.5 | 15.5 |
| 1200 | 1800 | 40:80 | 196 | 17.3 | 13.4 | 13.4 |
| 1800 | 1200 | 60:40 | 204 | 19.5 | 15.9 | 15.9 |

The above results and FIG. 2 (which shows the results obtained with injection moulding at 190° C.) demonstrate that there is a nonlinear relationship between the minimum dissolution temperature in molten polypropylene "RACO" MFR 70 g/10 min at a concentration of 3000 ppm and the weight ratio of the nucleators, namely MDBS and EDBS, in the blends. In addition, the trend in minimum dissolution temperature across the different blends of nucleators is generally followed by the trend in haze values of the polyolefin materials prepared using these blends of nucleators. The particular blend of nucleators exhibiting the lowest minimum dissolution temperature of those tested is consistently shown to give rise to the lowest haze value in the polyolefin material which is prepared. Furthermore, FIG. 2 also illustrates that a blend of MDBS and EDBS exhibits a lower minimum dissolution temperature in molten polypropylene "RACO" MFR 70 g/10 min, as well as a lower haze value in the resulting polyolefin material, than either of MDBS and EDBS individually, demonstrating synergy between these components at certain weight ratios.

Example 2

The minimum dissolution temperatures of MDBS, EDBS and blends thereof at a concentration of 3000 ppm in molten polypropylene "RACO" MFR 40 g/10 min were determined followed by determination of haze values for polypropylene materials prepared therefrom in accordance with the general procedure described above. The results are provided in Table 2 below.

TABLE 2

| MDBS (ppm) | EDBS (ppm) | MDBS: EDBS ratio | Min. Dissoln. Temp. (° C.) | Haze (ASTM-D1003-61 - 1 mm) | | |
|---|---|---|---|---|---|---|
| | | | | IM-180° C. | IM-190° C. | IM-200° C. |
| 0 | 3000 | 0:100 | 204 | 19.1 | 17.6 | 16.7 |
| 3000 | 0 | 100:0 | 209 | 20.3 | 15.2 | 11.3 |
| 300 | 2700 | 10:90 | 204 | 18.7 | 16.5 | 16.1 |
| 900 | 2100 | 30:70 | 203 | 18.2 | 14.7 | 14.7 |
| 1500 | 1500 | 50:50 | 205 | 18.2 | 16.7 | 15.0 |
| 2100 | 900 | 70:30 | 207 | 20.5 | 16.5 | 13.8 |
| 2700 | 300 | 90:10 | 209 | 20.1 | 16.4 | 12.5 |

The above results and FIG. 3 (which shows the results obtained with injection moulding at 190° C.) demonstrate that there is a nonlinear relationship between the minimum dissolution temperature in molten polypropylene "RACO" MFR 40 g/10 min at a concentration of 3000 ppm and the weight ratio of the nucleators, namely MDBS and EDBS, in the blends. In addition, the trend in minimum dissolution temperature across the different blends of nucleators is generally followed by the trend in haze values of the polyolefin materials prepared using these blends of nucleators. The particular blend of nucleators exhibiting the lowest minimum dissolution temperature of those tested is consistently shown to give rise to the lowest haze value in the polyolefin material which is prepared. Furthermore, FIG. 3 also illustrates that a blend of MDBS and EDBS exhibits a lower minimum dissolution temperature in molten polypropylene "RACO" MFR 40 g/10 min, as well as a lower haze value in the resulting polyolefin material, than either of MDBS and EDBS individually, demonstrating synergy between these components at certain weight ratios.

Example 3

The minimum dissolution temperatures of MDBS, EDBS and blends thereof at a concentration of 5000 ppm in molten polypropylene "RACO" MFR 70 g/10 min were determined followed by determination of haze values for polypropylene materials prepared therefrom in accordance with the general procedure described above. The results are provided in Table 3 below.

TABLE 3

| MDBS (ppm) | EDBS (ppm) | MDBS: EDBS ratio | Min. Dissoln. Temp. (° C.) | Haze (ASTM-D1003-61 - 1 mm) | | |
|---|---|---|---|---|---|---|
| | | | | IM-180° C. | IM-190° C. | IM-200° C. |
| 0 | 5000 | 0:100 | 213 | 26.0 | 18.7 | 14.8 |
| 5000 | 0 | 100:0 | 224 | 38.2 | 30.8 | 15.8 |
| 1500 | 3500 | 30:70 | 206 | 21.4 | 18.3 | 14.2 |
| 2000 | 3000 | 40:60 | 197 | 22.9 | 17.8 | 14.2 |
| 3000 | 2000 | 60:40 | 215 | 26.8 | 22.5 | 16.9 |

The above results and FIG. 4 (which shows the results obtained with injection moulding at 190° C.) demonstrate that there is a nonlinear relationship between the minimum dissolution temperature in molten polypropylene "RACO" MFR 70 g/10 mm at a concentration of 5000 ppm and the weight ratio of the nucleators, namely MDBS and EDBS, in the blends. In addition, the trend in minimum dissolution temperature across the different blends of nucleators is generally followed by the trend in haze values of the polyolefin materials prepared using these blends of nucleators. The particular blend of nucleators exhibiting the lowest minimum dissolution temperature of those tested is consistently shown to dye rise to the lowest haze value in the polyolefin material which is prepared. Furthermore, FIG. 4 also illustrates that a blend of MDBS and EDBS exhibits a lower minimum dissolution temperature in molten polypropylene "RACO" MFR 70 g/10 min, as well as a lower haze value in the resulting polyolefin material, than either of MDBS and EDBS individually, demonstrating synergy between these components at certain weight ratios.

Example 4

The minimum dissolution temperatures of 3,4-DMDMS, MDBS and blends thereof at a concentration of 3000 ppm in molten polypropylene "RACO" MFR 70 g/10 min were determined followed by determination of haze values for polypropylene materials prepared therefrom in accordance with the general procedure described above. The results are provided in Table 4 below.

TABLE 4

| 3,4-DMDBS (ppm) | MDBS (ppm) | 3,4-DMDBS: MDBS ratio | Min. Dissoln. Temp. (° C.) | Haze (ASTM-D1003-61 - 1 mm) | | |
|---|---|---|---|---|---|---|
| | | | | IM-180° C. | IM-190° C. | IM-200° C. |
| 0 | 3000 | 0:100 | 211 | 21.8 | 18.5 | 18.5 |
| 3000 | 0 | 100:0 | 224 | 38.9 | 37.6 | 37.6 |
| 900 | 2100 | 30:70 | 200 | 17.1 | 11.5 | 11.5 |
| 1200 | 1800 | 40:60 | 203 | 19.5 | 13.3 | 13.3 |
| 1800 | 1200 | 60:40 | 207 | 22.2 | 18.4 | 18.4 |

The above results and FIG. 5 (which shows the results obtained with injection moulding at 190° C.) demonstrate that there is a nonlinear relationship between the minimum dissolution temperature in molten polypropylene "RACO" MFR 70 g/10 min at a concentration of 3000 ppm and the weight ratio of the nucleators, namely 3,4-DMDBS and MDBS, in the blends. In addition, the trend in minimum dissolution temperature across the different blends of nucleators is generally followed by the trend in haze values of the polyolefin materials prepared using these blends of nucleators. The particular blend of nucleators exhibiting the lowest minimum dissolution temperature of those tested is consistently shown to give rise to the lowest haze value in the polyolefin material which is prepared. Furthermore, FIG. 5 also illustrates that a blend of MDBS and EDBS exhibits a lower minimum dissolution temperature in molten polypropylene "RACO" MFR 70 g/10 min, as well as a lower haze value in the resulting polyolefin material, than either of 3,4-DMDBS and MDBS individually, demonstrating synergy between these components at certain weight ratios.

Example 5

The minimum dissolution temperatures of 3,4-DMDMS, MDBS and blends thereof at a concentration of 3000 ppm in molten polypropylene "RACO" MFR 40 g/10 min were determined followed by determination of haze values for polypropylene materials prepared therefrom in accordance with the general procedure described above. The results are provided in Table 5 below.

TABLE 5

| 3,4-DMDBS (ppm) | MDBS (ppm) | 3,4-DMDBS: MDBS ratio | Min. Dissoln. Temp. (° C.) | Haze (ASTM-D1003-61 - 1 mm) | | |
|---|---|---|---|---|---|---|
| | | | | IM-180° C. | IM-190° C. | IM-200° C. |
| 0 | 3000 | 0:100 | 209 | 19.5 | 13.0 | 9.4 |
| 3000 | 0 | 100:0 | 226 | 37.4 | 28.8 | 21.3 |
| 300 | 2700 | 10:90 | 208 | 25.0 | 12.5 | 8.7 |
| 900 | 2100 | 30:70 | 203 | 18.8 | 8.5 | 7.9 |
| 1500 | 1500 | 50:50 | 205 | 21.1 | 12.4 | 7.4 |
| 2100 | 900 | 70:30 | 215 | 24.6 | 20.3 | 13.8 |
| 2700 | 300 | 90:10 | 224 | 34.2 | 25 | 14.1 |

The above results and FIG. 6 (which shows the results obtained with injection moulding at 190° C.) demonstrate that there is a nonlinear relationship between the minimum dissolution temperature in molten polypropylene "RACO" MFR 40 g/10 min at a concentration of 3000 ppm and the weight ratio of the nucleators, namely 3,4-DMDBS and MDBS, in the blends. In addition, the trend in minimum dissolution temperature across the different blends of nucleators is generally followed by the trend in haze values of the polyolefin materials prepared using these blends of nucleators. The particular blend of nucleators exhibiting the lowest minimum dissolution temperature of those tested is consistently shown to give rise to the lowest haze value in the polyolefin material which is prepared. Furthermore, FIG. 6 also illustrates that a blend of 3,4-DMDBS and MDBS exhibits a lower minimum dissolution temperature in molten polypropylene "RACO" MFR 40 g/10 min, as well as a lower haze value in the resulting polyolefin material, than either of 3,4-DMDBS and MDBS individually, demonstrating synergy between these components at certain weight ratios.

Example 6

The minimum dissolution temperatures of 3,4-DMDBS, MDBS and blends thereof at a concentration of 5000 ppm in molten polypropylene "RACO" MFR 70 g/10 min were determined followed by determination of haze values for polypropylene materials prepared therefrom in accordance with the general procedure described above. The results are provided in Table 6 below.

TABLE 6

| 3,4-DMDBS (ppm) | MDBS (ppm) | 3,4-DMDBS: MDBS ratio | Min. Dissoln. Temp. (° C.) | Haze (ASTM-D1003-61 - 1 mm) | | |
|---|---|---|---|---|---|---|
| | | | | IM-180° C. | IM-190° C. | IM-200° C. |
| 0 | 5000 | 0:100 | 224 | 38.2 | 30.8 | 15.8 |
| 5000 | 0 | 100:0 | 235 | 47.3 | 45 | 40.5 |
| 1500 | 3500 | 30:70 | 214 | 33.7 | 24.9 | 14.3 |
| 2000 | 3000 | 40:60 | 216 | 35.1 | 27.4 | 13.6 |
| 3000 | 2000 | 60:40 | 228 | 35.9 | 27.3 | 20.6 |

The above results demonstrate that there is a nonlinear relationship between the minimum dissolution temperature in molten polypropylene "RACO" MFR 70 g/10 min at a concentration of 5000 ppm and the weight ratio of the nucleators, namely 3,4-DMDBS and MDBS, in the blends. In addition, the trend in minimum dissolution temperature across the different blends of nucleators is generally followed by the trend in haze values of the polyolefin materials prepared using these blends of nucleators.

Example 7

The minimum dissolution temperatures of 3,4-DMDBS, EDBS and blends thereof at a concentration of 3000 ppm in molten polypropylene "RACO" MFR 70 g/10 min were determined followed by determination of haze values for polypropylene materials prepared therefrom in accordance with the general procedure described above. The results are provided in Table 7 below.

TABLE 7

| 3,4-DMDBS (ppm) | MDBS (ppm) | 3,4-DMDBS: MDBS ratio | Min. Dissoln. Temp. (°C.) | Haze (ASTM-D1003-61 - 1 mm) | | |
|---|---|---|---|---|---|---|
| | | | | IM-180° C. | IM-190° C. | IM-200° C. |
| 0 | 3000 | 0:100 | 206 | 17.8 | 15.1 | 15.1 |
| 3000 | 0 | 100:0 | 224 | 38.9 | 37.6 | 37.6 |
| 900 | 2100 | 30:70 | 196 | 17.6 | 12.7 | 12.7 |
| 1200 | 1800 | 40:60 | 197 | 17.4 | 15.6 | 15.6 |
| 1500 | 1500 | 50:50 | 199 | 20.5 | 17.5 | 17.5 |

Figure 7:
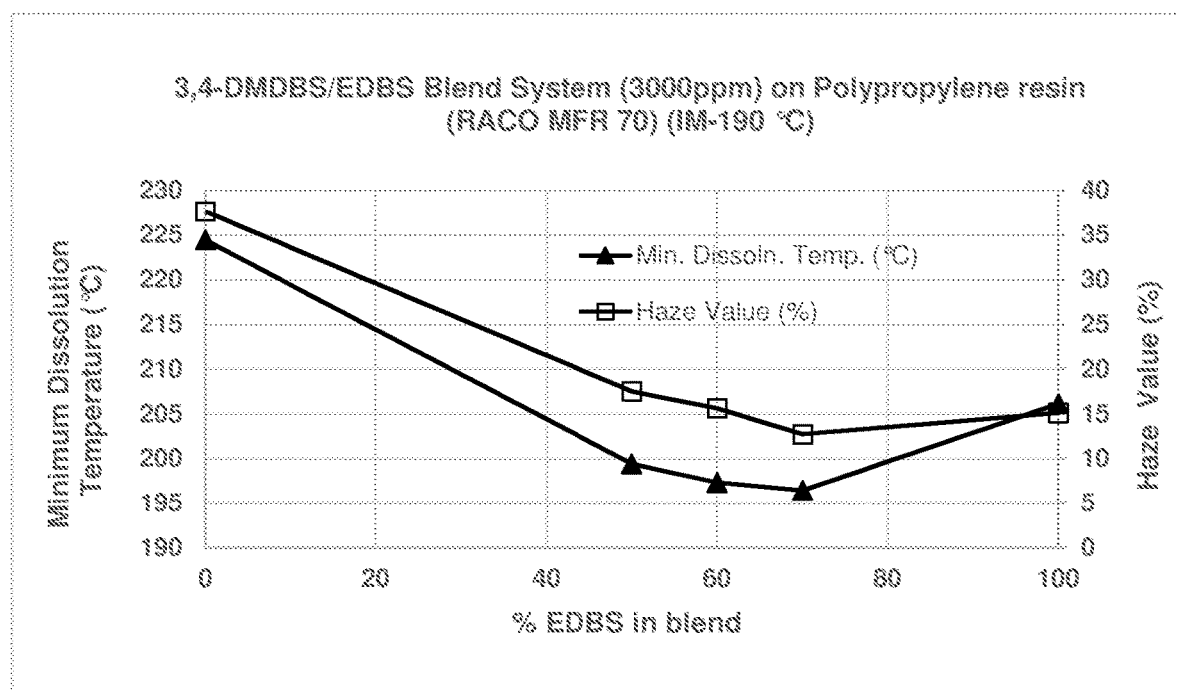

The above results and FIG. 7 (which shows the results obtained with injection moulding at 190° C.) demonstrate that there is a nonlinear relationship between the minimum dissolution temperature in molten polypropylene "RACO" MFR 70 g/10 min at a concentration of 3000 ppm and the weight ratio of the nucleators, namely 3,4-DMDBS and EDBS, in the blends. In addition, the trend in minimum dissolution temperature across the different blends of nucleators is generally followed by the trend in haze values of the polyolefin materials prepared using these blends of nucleators. The particular blend of nucleators exhibiting the lowest minimum dissolution temperature of those tested is consistently shown to give rise to the lowest haze value in the polyolefin material which is prepared. Furthermore, FIG. 7 also illustrates that a blend of 3,4-DMDBS and EDBS exhibits a lower minimum dissolution temperature in molten polypropylene "RACO" MFR 70 g/10 min, as well as a lower haze value in the resulting polyolefin material, than either of 3,4-DMDBS and EDBS individually, demonstrating synergy between these components at certain weight ratios.

What is claimed is:

1. A method for identifying a blend of at least two nucleators having a weight ratio of components that provides reduced haze in a nucleated polyolefin material compared to blends of the same nucleators having different weight ratios of components, wherein each nucleator is soluble in a molten polyolefin resin, said method comprising the steps of:
   i) preparing a plurality of blends of the at least two nucleators wherein each blend contains the same at least two nucleators but in a different weight ratio, wherein the plurality of blends includes one or more blends in which one of the at least two nucleators is a major weight fraction of the blend as well as one or more blends in which the same one of the at least two nucleators is a minor weight fraction of the blend, wherein the at least two nucleators are selected from substituted dibenzylidene sorbitol derivatives; 1,3,5-benzenetrisamides; trans- or dimethyl-quinacridone; and N,N'-di-$C_5$-$C_6$cycloalkyl-2,6-naphthalene dicarboxamides;
   ii) determining, for each of the blends prepared in step i), a minimum dissolution temperature at which a given concentration of each of the blends becomes completely dissolved in individual samples of the same molten polyolefin resin, wherein the concentration of each of the different blends in the individual samples is substantially the same and below the saturation point in the molten polyolefin resin and the same method for determining the minimum dissolution temperature is used for each blend, and wherein the polyolefin resin is selected from polyethylene resins, polypropylene resins, polybutylene resins, or blends or copolymers thereof; and
   iii) identifying a blend of the at least two nucleators which has a minimum dissolution temperature which is lower than that determined in step ii) for a majority of the plurality of blends.

2. A method according to claim 1, wherein the blend identified in step iii) corresponds to a minima in a plot of minimum dissolution temperature against weight fraction of the components of the blends based on the minimum dissolution temperatures determined for each of the plurality of blends in step ii).

3. A method according to claim 1, wherein the blend identified corresponds to a blend of the plurality of blends having the lowest minimum dissolution temperature.

4. A method according to claim 1, wherein a) the minimum dissolution temperature for each blend in step ii) is determined by optical microscopy, light scattering or differential scanning calorimetry, employing controlled rate heating of a mixture of the blend and the molten polyolefin resin sample and/or b) wherein determining the minimum dissolution temperature for each blend in step ii) involves controlled rate heating of a mixture of the blend and the molten polyolefin resin sample without any shear being applied to the mixture.

5. A method according to claim 1, wherein the minimum dissolution temperature for each blend in step ii) is determined by an optical microscopy method comprising:
   a) melt compounding each blend of the at least two nucleators with a polyolefin resin sample to form a compounded composition comprising the blend of the at least two nucleators at a concentration of at least 500 ppmw, without dissolving the blend in the polyolefin resin;
   b) raising the temperature of the composition at a controlled rate whilst continuously obtaining microscope images of the composition using a microscope with a light source configured to transmit light through the composition, a heating platform configured to heat the composition and an image capturing device configured to continuously capture microscope images of the composition, wherein the image capturing device is in communication with an analysis unit configured to determine the brightness of the captured images and brightness variability between successive captured images;
   c) determining the temperature of the composition at which a peak in relative brightness variability is observed based on analysis of the captured images and thereby obtaining the minimum dissolution temperature.

6. A method according to claim 1, wherein a) the blends contain two or three different nucleators only; and/or b) wherein the plurality of blends includes at least 3, at least 5, or at least 10, different blends.

7. A method according to claim 1, wherein there is a nonlinear relationship between the minimum dissolution temperature and the weight ratio of the nucleators in the blend.

8. A method according to claim 1, wherein the blends contain two nucleators only and wherein the plurality of blends includes blends having weight ratios evenly distributed across an individual nucleator concentration range of above 0 wt. % to below 100 wt. %.

9. A method according to claim 1, wherein the concentration of each blend of the at least two nucleators in the individual polyolefin resin sample is 5000 ppmw of less; is from 500 ppmw to 5000 ppmw; is from 1500 ppmw to 4000 ppmw; is from 1500 ppmw to 2500 ppmw; is from 1750 ppmw to 2250 ppmw; is from 1900 ppmw to 2100 ppmw; is from 2250 ppmw to 3250 ppmw; or is from 2500 ppmw to 3000 ppmw.

10. A method according to claim 1, further comprising determining the minimum dissolution temperature for each nucleator of the plurality of blends individually in the polyolefin resin, wherein the total concentration of nucleator in the polyolefin resin sample used to determine the minimum dissolution temperature for each nucleator individually is substantially the same as that used for determining the minimum dissolution temperature of each of the plurality of blends, and wherein the same method for determining the minimum dissolution temperature for each of the plurality of blends is used for determining that of the nucleators of the plurality of blends individually.

11. A method according to claim 10, wherein the blend of nucleators identified in step iii) has a minimum dissolution temperature which is lower than at least one, or all, of the nucleators present in the blend individually.

12. A method according to claim 1, wherein the blend identified in step iii) is used to prepare a nucleated polyolefin material which has a lower haze value, as measured in accordance with ASTM D1003-61 for a 1 mm thick plaque, compared to a nucleated polyolefin material prepared from any of the nucleators of the blend used individually, when and substantially the same total nucleator concentration is used in preparing the polyolefin materials.

13. A method according to claim 1, wherein the nucleators of the blends are selected from substituted dibenzylidene sorbitol derivatives; 1,3,5-benzenetrisamides; trans- or dimethyl-quinacridone; and N,N'-di-$C_5$-$C_8$-cycloalkyl-2,6-naphthalene dicarboxamides; wherein the substituted dibenzylidene sorbitol derivatives are selected from those according to Formula I below:

Formula I

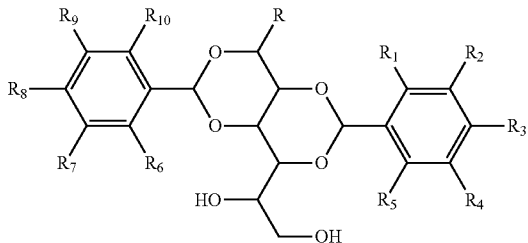

wherein $R_1$, $R_2$, $R_3$, $R_4$, $R_5$, $R_6$, $R_7$, $R_8$, $R_9$, $R_{10}$ are the same or different and are selected from hydrogen, $C_1$ to $C_8$ alkyl, $C_1$ to $C_4$ alkoxy, $C_1$ to $C_4$ alkoxycarbonyl, halogen, hydroxy, $C_1$ to $C_6$ alkylthio, $C_1$ to $C_6$ alkylsulfoxy, provided that at least one of $R_1$ to $R_{10}$ is other than hydrogen; and R is selected from hydrogen, $C_1$ to $C_8$ alkyl, $C_2$ to $C_8$ alkenyl, $C_1$ to $C_8$ alkoxy, $C_1$ to $C_8$ alkylhydroxy, and $C_1$ to $C_8$ haloalkyl.

14. A method according to claim 13, wherein:
a) the substituted dibenzylidene sorbitol derivatives are selected from bis-p-methylbenzylidene sorbitol, di(p-chlorobenzylidene) sorbitol, di(o-methylbenzylidene) sorbitol, bis-p-ethylbenzylidene sorbitol, bis(3,4-dimethylbenzylidene) sorbitol, and bis(3,4-diethylbenzylidene) sorbitol, and bis(4-propylbenzylidene) propylsorbitol
b) wherein the 1,3,5-benzenetrisamides are selected from N-[3,5-Bis-(2,2-dimethylpropionylamino)-phenyl]-2,2-dimethylpropionamide and N,N',N"-Tris(2-methylcyclohexyl) 1,2,3-propanetricarboxamide; and/or
c) wherein the N,N'-di-$C_5$-$C_8$-cycloalkyl-2,6-naphthalene dicarboxamide is selected from N,N'-dicyclohexyl-2,6-naphthalene dicarboxamide and N,N'-dicyclooctyl-2,6-naphthalene dicarboxamide.

15. A method according to claim 1, wherein the method further comprises a step iv) of preparing a nucleated polyolefin material using the blend identified in step iii) by preparing a polyolefin resin composition comprising the at least two nucleators in the weight ratio according to the blend identified in step iii) and processing said polyolefin resin composition to form said polyolefin material.

16. A method according to claim 15, wherein processing of the polyolefin resin composition comprises injection and/or extrusion moulding the polyolefin resin composition.

17. A method according to claims 15, wherein processing of the polyolefin resin composition to form said polyolefin material is conducted at a temperature of from 180° C. to 200° C., from 185° C. to 198° C., from 190° C. to 197° C., or from 190° C. to 195° C.

18. A method according to claim 15, wherein: a) the nucleated polyolefin material has a haze value, as measured in accordance with ASTM D1003-61 for a 1 mm thick plaque, of below 20%, below 15%, below 13%, or below 12%; and/or b) wherein the nucleated polyolefin material has a Yellowness index, as measured in accordance with ASTM E313 for a 2 mm thick plaque, of less than 7.5, than 5.0, less than 2.5, or less than 0.5.

19. A polyolefin material obtainable by the method of claim 15, wherein the at least two nucleators are selected from substituted dibenzylidene sorbitol derivatives; 1,3,5-benzenetrisamides; trans- or dimethyl-quinacridone; and N,N'-di-$C_5$-$C_6$cycloalkyl-2,6-naphthalene dicarboxamides substituted dibenzylidene sorbitol derivatives;
wherein the blend of nucleators has a minimum dissolution temperature which is lower than all of the nucleators present in the blend individually;
wherein, as part of identifying a blend of nucleators in step iii) of the method, at least 5 different blends are tested, the different blends having weight ratios evenly distributed across an individual nucleator concentration range of above 0 wt. % to below 100 wt. %;
wherein the blend identified in step iii) corresponds to a minima in a plot of minimum dissolution temperature against weight fraction of the components of the blends based on the minimum dissolution temperatures determined for each of the plurality of blends in step ii); and
wherein the polyolefin resin used is selected from polyethylene resins, polypropylene resins, polybutylene resins, or blends or copolymers thereof.

20. A method for identifying a blend of at least two nucleators having a weight ratio of components that provides reduced haze in a nucleated polyolefin material compared to blends of the same nucleators having different weight ratios of components, wherein each nucleator is soluble in a molten polyolefin resin, said method comprising the steps of:

i) preparing a plurality of blends of the at least two nucleators wherein each blend contains the same at least two nucleators but in a different weight ratio, wherein each of the plurality of blends of the at least two nucleators includes the same one nucleator as a major weight fraction of the blend, wherein the at least two nucleators are selected from substituted dibenzylidene sorbitol derivatives; 1,3,5-benzenetrisamides; trans- or dimethyl-quinacridone; and N,N'-di-C5-C6cycloalkyl-2,6-naphthalene dicarboxamides;

ii) determining, for each of the blends prepared in step i), a minimum dissolution temperature at which a given concentration of each of the blends becomes completely dissolved in individual samples of the same molten polyolefin resin, wherein the concentration of each of the different blends in the individual samples is substantially the same and below the saturation point in the molten polyolefin resin and the same method for determining the minimum dissolution temperature is used for each blend, and wherein the polyolefin resin is selected from polyethylene resins, polypropylene resins, polybutylene resins, or blends or copolymers thereof; and iii) identifying a blend of the at least two nucleators which has a minimum dissolution temperature which is lower than that determined in step ii) for a majority of the plurality of blends.

* * * * *